US009224031B2

United States Patent
Glensbjerg et al.

(10) Patent No.: US 9,224,031 B2
(45) Date of Patent: Dec. 29, 2015

(54) COMPACT DARK FIELD LIGHT SOURCE AND DARK FIELD IMAGE ANALYSIS AT LOW MAGNIFICATION

(75) Inventors: Martin Glensbjerg, Brønshøj (DK); Johan Christer Holm, Søborg (DK); Frans Ejner Ravn, Frederiksberg (DK); Søren Kjaerulff, Hillerød (DK)

(73) Assignee: ChemoMetec A/S, Allerød (DK)

( * ) Notice: Subject to any disclaimer, the term of this patent is extended or adjusted under 35 U.S.C. 154(b) by 265 days.

(21) Appl. No.: 13/699,042

(22) PCT Filed: May 18, 2011

(86) PCT No.: PCT/DK2011/050166
§ 371 (c)(1),
(2), (4) Date: Feb. 4, 2013

(87) PCT Pub. No.: WO2011/144212
PCT Pub. Date: Nov. 24, 2011

(65) Prior Publication Data
US 2013/0129181 A1  May 23, 2013

(30) Foreign Application Priority Data
May 21, 2010  (DK) .................................. 2010 70211

(51) Int. Cl.
*G06K 9/00* (2006.01)
*G02B 21/12* (2006.01)
(Continued)

(52) U.S. Cl.
CPC ........ *G06K 9/00147* (2013.01); *G01N 15/1475* (2013.01); *G01N 21/6458* (2013.01);
(Continued)

(58) Field of Classification Search
CPC ............ G06T 5/50; G06T 2207/10056; G06T 2207/10064; G06T 2207/30024; G02B 21/14; G02B 21/125; G02B 21/12; G02B 21/10
USPC .................................................. 382/133, 134
See application file for complete search history.

(56) References Cited

U.S. PATENT DOCUMENTS 2,674,157 A * 4/1954 Heine .......................... 359/370
4,896,966 A   1/1990 Boisseau et al.
(Continued)

FOREIGN PATENT DOCUMENTS

EP    1486812 A2   12/2004
EP    1738212 A2    1/2007
(Continued)

OTHER PUBLICATIONS

"Olympus BX51 BX2 Series Brochure." Olympus FluoView Resource Center . Olympus, Feb. 2004. Web. Feb. 5, 2015. <http://olympusfluoview.com/brochures/pdfs/bx51.pdf>.*
(Continued)

Primary Examiner — Michael A Newman
(74) Attorney, Agent, or Firm — Dinsmore & Shohl LLP

(57) ABSTRACT

The invention relates to image analysis of dark field images obtained at low magnification below 10:1. Image analysis of dark field images obtained at low magnification can be combined with analyzes of images obtained in respect of the same section of a sample and same magnification but with other techniques such as fluorescent microscopy. The system and method can be used e.g. for particle counting, particle size measurement, particle size distribution, morphology measurement, where the particles can be cells and/or cell parts. The invention also relates to a compact dark field light source unit, a system or apparatus including a microscope which by itself is compact and comprises the mentioned dark field light source unit.

49 Claims, 21 Drawing Sheets

Figure 1:
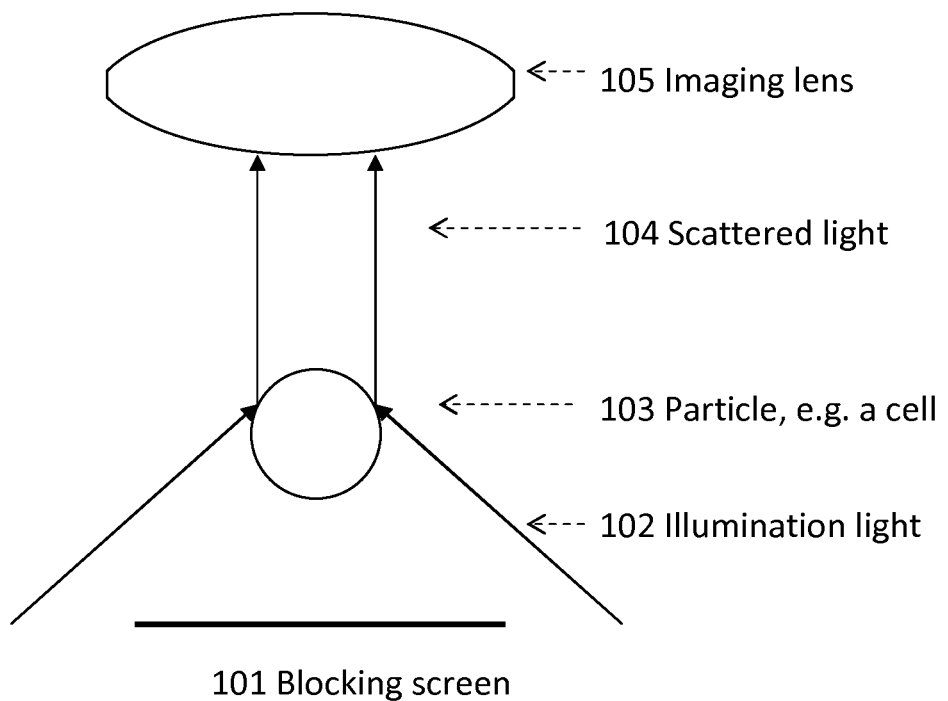

(51) Int. Cl.
 G01N 15/14    (2006.01)
 G02B 21/10    (2006.01)
 G01N 21/64    (2006.01)
(52) U.S. Cl.
 CPC .............. *G02B21/10* (2013.01); *G02B 21/125* (2013.01); *G01N 2015/1486* (2013.01); *G01N 2015/1497* (2013.01); *G06T 2207/10056* (2013.01); *G06T 2207/30024* (2013.01)

(56) References Cited

U.S. PATENT DOCUMENTS

| | | | |
|---|---|---|---|
| 4,896,967 | A * | 1/1990 | Douglas-Hamilton et al. ............................ 382/128 |
| 5,724,139 | A * | 3/1998 | Guerra ........................... 356/600 |
| 6,195,451 | B1 | 2/2001 | Kerschmann et al. |
| 7,272,252 | B2 * | 9/2007 | De La Torre-Bueno et al. ............................ 382/133 |
| 2004/0061070 | A1 | 4/2004 | Hansen |
| 2005/0237605 | A1 * | 10/2005 | Vodyanoy et al. ............ 359/385 |
| 2007/0014002 | A1 * | 1/2007 | Vodyanoy et al. ............ 359/387 |
| 2007/0139764 | A1 * | 6/2007 | Vodyanoy et al. ............ 359/389 |
| 2007/0242336 | A1 * | 10/2007 | Vodyanoy et al. ............ 359/234 |
| 2008/0225278 | A1 * | 9/2008 | Namba et al. ................. 356/123 |
| 2010/0246927 | A1 * | 9/2010 | Arbuckle ...................... 382/133 |

FOREIGN PATENT DOCUMENTS

| | | |
|---|---|---|
| JP | 9043147 A | 2/1997 |
| WO | 2005101086 A2 | 10/2005 |
| WO | 2009126685 A2 | 10/2009 |

OTHER PUBLICATIONS

Gibbs-Flournoy, et al. "Darkfield-Confocal Microscopy Detection of Nanoscale Particle Internalization by Human Lung Cells." Particle and Fibre Toxicology 8.2 (2011): 1-11. Print.*

Mortensen et al., Functionalization and Cellular Uptake of Boron Carbide Nanoparticles. The First Step Toward T Cell-Guided Boron Neutron Capture Therapy, Bioconjugate Chem, 2006, pp. 284-290, vol. 17, American Chemical Society.

* cited by examiner

COMPACT DARK FIELD LIGHT SOURCE AND DARK FIELD IMAGE ANALYSIS AT LOW MAGNIFICATION

CROSS-REFERENCE TO RELATED APPLICATIONS

This application is the U.S. National Phase of PCT/DK2011/050166 filed May 18, 2011, which claims priority of Danish Patent Application PA 2010 70211 filed May 21, 2010.

All patent and non-patent references cited in the present application, are hereby incorporated by reference in their entirety.

FIELD OF INVENTION

The invention relates to image analysis of dark field images obtained at low magnification below 10:1. Image analysis of dark field images obtained at low magnification can be combined with analysis or analyses of images obtained in respect of the same section of a sample and same magnification but with other techniques such as fluorescent microscopy. The system and method can be used e.g. for particle counting, particle size measurement, particle size distribution, morphology measurement, where the particles can be cells and/or cell parts. The invention also relates to a compact dark field light source unit, a system or apparatus including a microscope which by itself is compact and comprises the mentioned dark field light source unit.

BACKGROUND OF INVENTION

Easy, fast and precise detection of particles such as cells is an important process in different fields e.g. at hospitals, companies working with bioreactors, cell research, drug discovery, breweries, dairies, breeding stations etc. On the market is a cell counting system "Nucleocounter NC-3000" (ChemoMetec, Allerød, Denmark) which is a small unit of 29×29×31 cm (H×W×D) including a full microscope and a sample entrance. The unit is connected to a computer comprising an image analyzing software. The NC-3000 system enables fast and precise automated detection at low magnification of cells by specific counting of nuclei, giving reproducible and accurate counts based on analyses performed with a fluorescence microscope.

The "NC-3000" can be used for viability and cell count, cell-cycle assay, mitochondrial potential assay, vitality assay, quantification of fluorescence intensity, fluorescence measurements from violet to far red, DNA fragmentation assay and GFP transfection efficiency assay.

Different microscope illumination techniques give different information in respect of a sample which is analyzed.

The inventors of the present invention have surprisingly found a solution of how to create and use a dark field light source unit which by itself is compact and which can be used in a compact microscope system such as the "Nucleocounter NC-3000" system and which is based on performing analyses at low magnification.

SUMMARY OF INVENTION

An aspect of the invention relates to an apparatus for analysing a sample comprising particles such as cells and/or cell parts and wherein the analysis is performed at low magnification, the apparatus comprises At least one dark field light source, At least one other light source, An image sensor for obtaining images of a sample, and Magnifying means capable of projecting an image of the particles on the image sensor at a magnification below 10:1, wherein light in said at least one dark field light source and said at least one other light source is obtained from LED and/or a laser diode.

It has surprisingly turned out that by using the apparatus or system as described herein it is possible to perform image analysis including at least one image obtained by dark field microscopy at a low magnification below 10:1. The contrast of the dark field images are high, hereby making it possible to perform image analysis by comparing images obtained by different techniques of the same section of a sample The obtained images may be used for image analysis. In a preferred embodiment the image analysis of the apparatus is performed in respect of at least two images obtained by dark field analysis or at least one image obtained by dark field analysis and at least one image obtained by fluorescence analysis.

In a preferred embodiment when utilising the apparatus the at least one image obtained by dark field analysis and the at least one image obtained by fluorescence analysis are paired in the image analysis system such that particles such as cells and/or cell parts with at least one predetermined feature are identified in one of the techniques dark field or fluorescence, and these identified particles such as cells and/or cell parts with at least one predetermined feature are discriminated when performing an image analysis of at least one image obtained with the other of the techniques dark field or fluorescence.

Particles such as cells and/or cell parts which can be discriminated in an image analysis may be particles with a size below and/or above one or more predetermined sizes. With a determination of particles to be discriminated in an image obtained in one technique e.g. in dark field, these particles can be discriminated when analysing at least one image obtained in the other technique e.g. by fluorescence. In a preferred embodiment particles identified by dark field and which are to be discriminated can be removed in the analysis of at least one fluorescence image. Thereby one can obtain an analysis of those particles fulfilling certain criteria(s). In another preferred embodiment the particles to be discriminated are identified by fluorescence, and at least one dark field image is analysed with the identified particles discriminated.

Also described is a method of performing image analysis of images including dark field images obtained at low magnification.

Further described is a dark field light source unit for use in microscopy with a magnification below 10:1, the light source unit comprises at least one light source for emitting light rays, at least one light guide for guiding the light rays emitted from the light source, at least one light directing device for deflecting light rays guided by the light guide, a blocking screen for blocking light rays emitted from the light source and for blocking light rays which are not guided by the light guide.

DEFINITIONS

The following terms have the meanings set forth below:

Acceptance angle: is used in its conventional meaning, i.e., the maximum angle for which a focusing means (e.g. collimating lens of FIG. 2) can collect signals to be detected by the detection means.

Detection area: the area of the surface of the sample to be detected by one detection, often in the form of an image collected by a CCD.

Detector-sample axis: the axis from the detector to the sample.

Direct light path axis: the axis from the centre of the light beam to the sample plane when direct lighting is used, which is exemplified by the centre of a light emitting diode.

Incidence angle: the angle between the main light path and the detection-sample axis in the case of direct light and the angle between the main light path of the light deflected by a light deflecting device and the direct light path axis.

Light guide angle: the angle between the light path in the light guide and the direct light path axis.

Light means: the light system comprising all the light sources for exposing onto one side of the sample.

Magnification: is the absolute value of the transverse magnification of the optical system between the sample and the detection plane. It is described as a linear magnification/enlargement indicating the linear dimension of the detection plane in relation to the linear dimension of the particle analysed, e.g. 4:1 means that a linear dimension of a particle is obtained as a linear dimension at the detection plane which is four time the linear dimension of the particle.

Sample plane: the plane perpendicular to the detector-sample axis or perpendicular to the direct light path axis and whereupon the sample is arranged.

SHORT DESCRIPTION OF DRAWINGS

Figure 2:
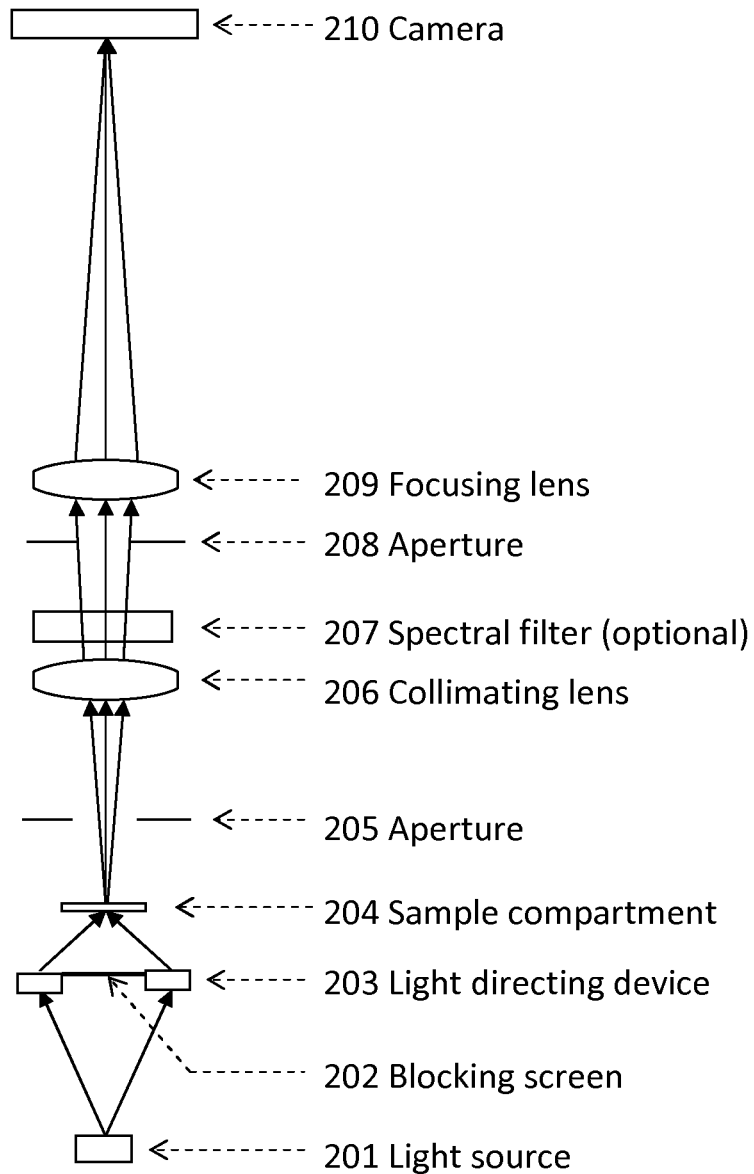
Figure 3:
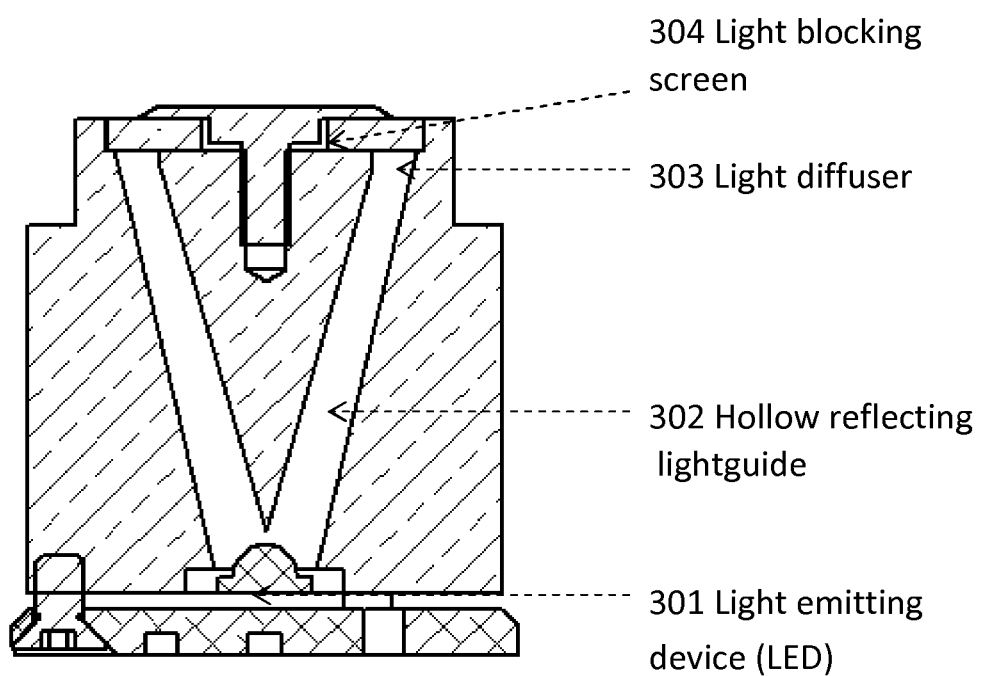
Figure 4:
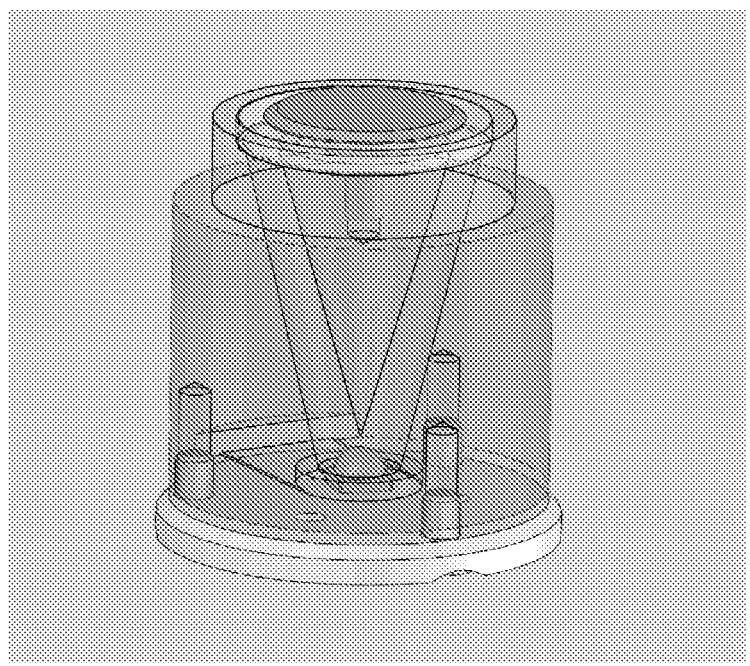
Figure 5:
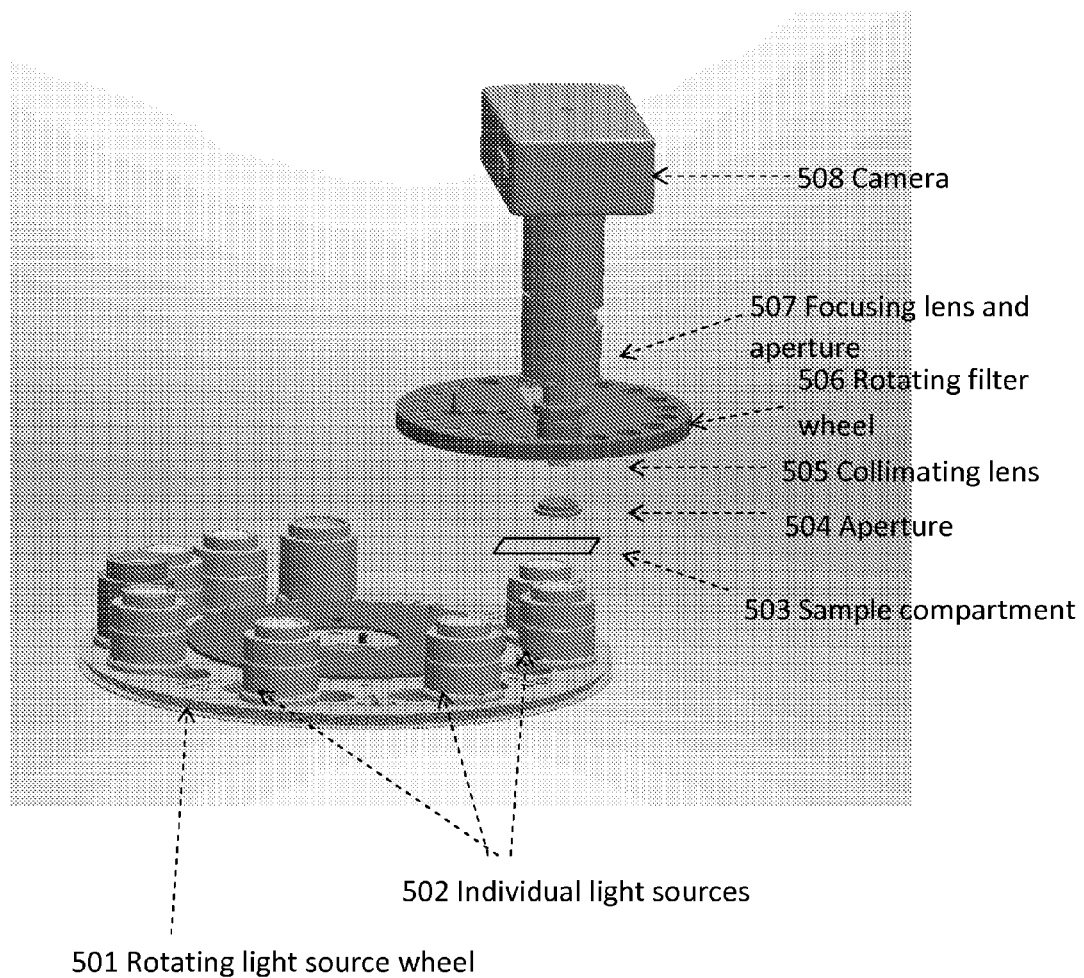
Figure 6:
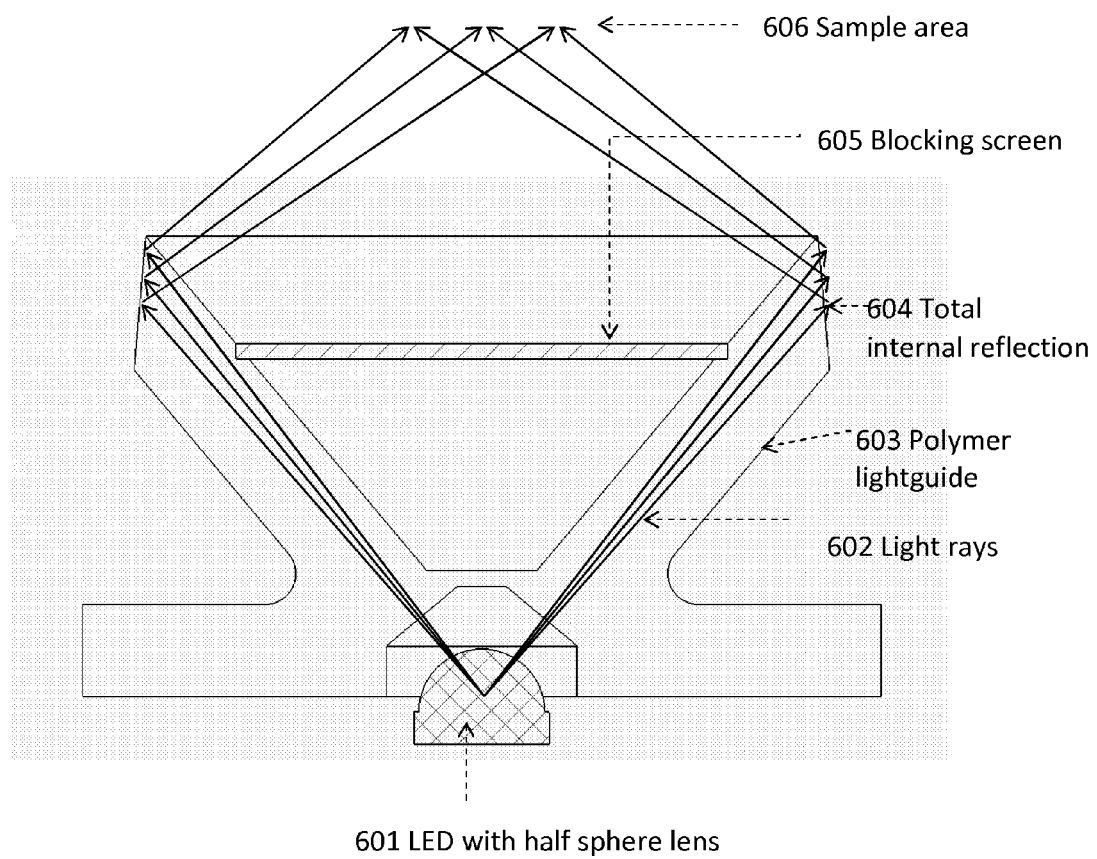
Figure 7:
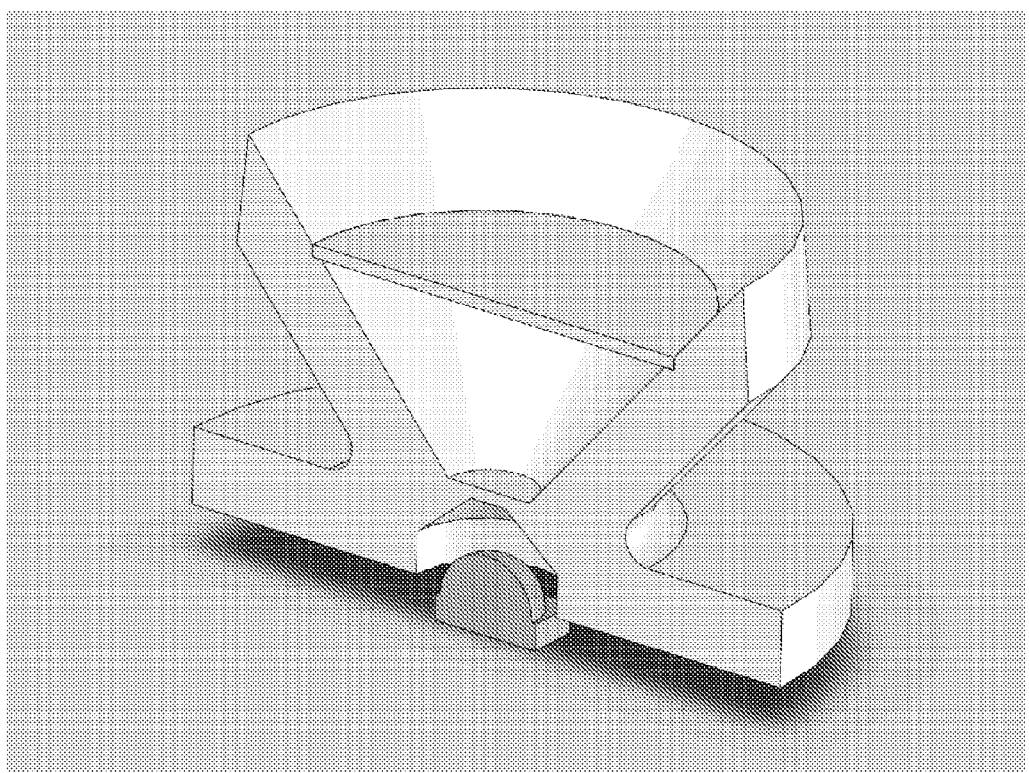
Figure 8:
Figure 9:
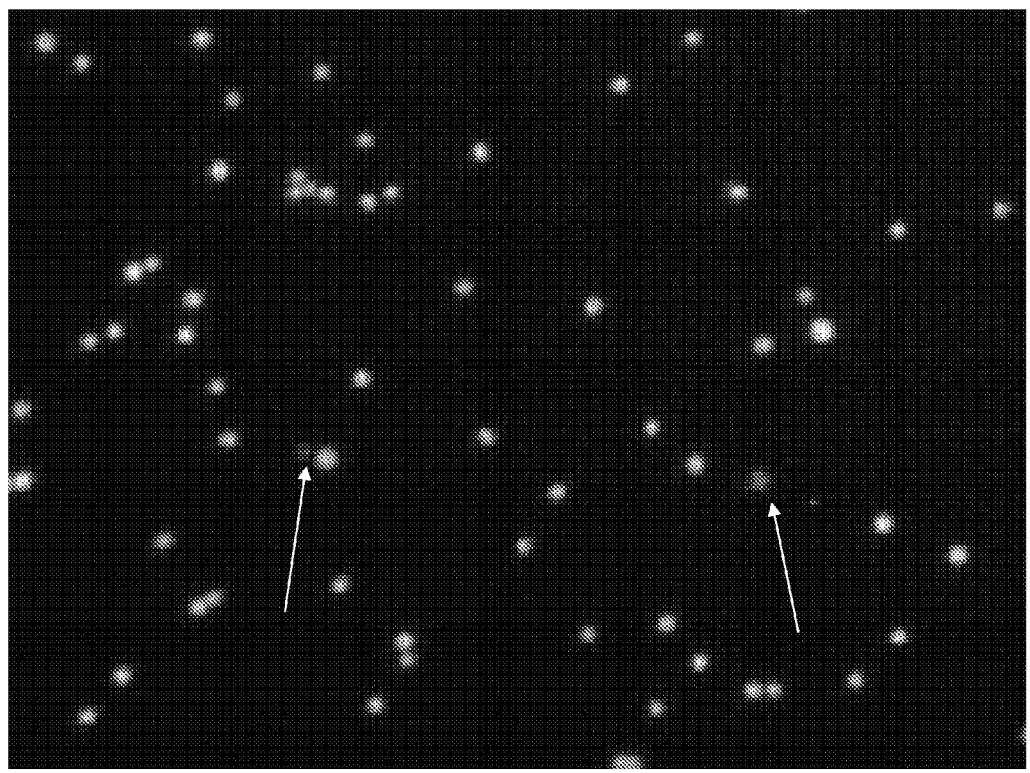
Figure 10:
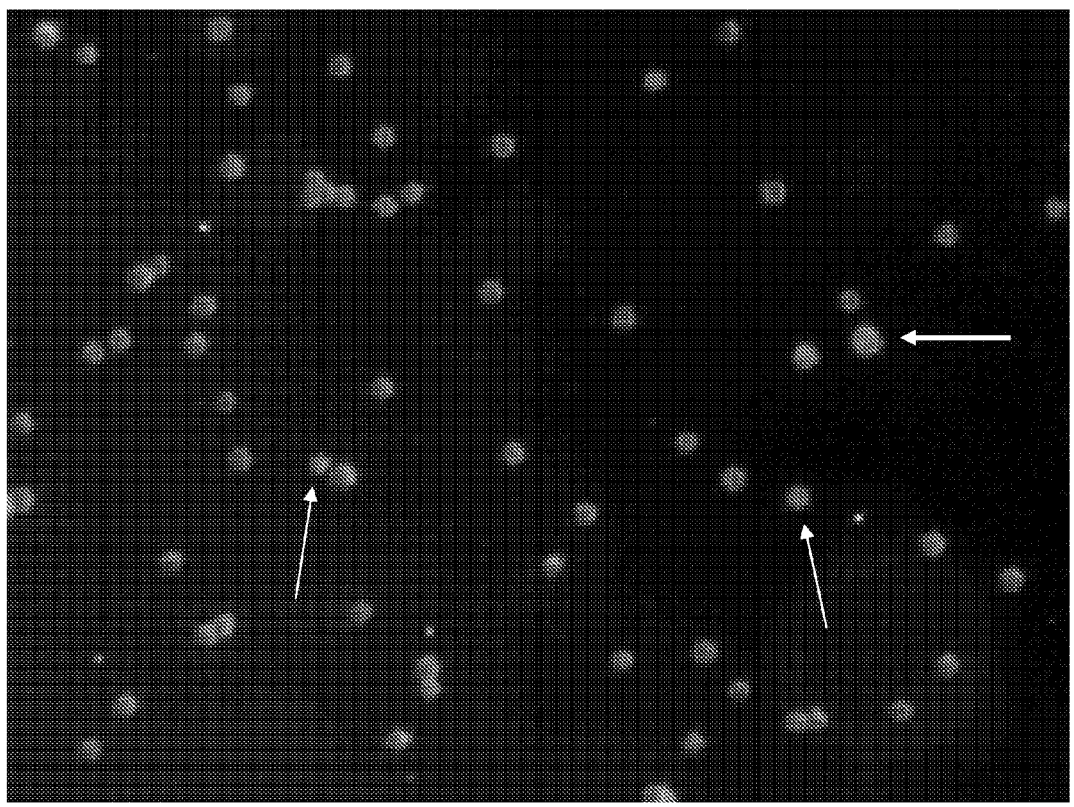
Figure 11:
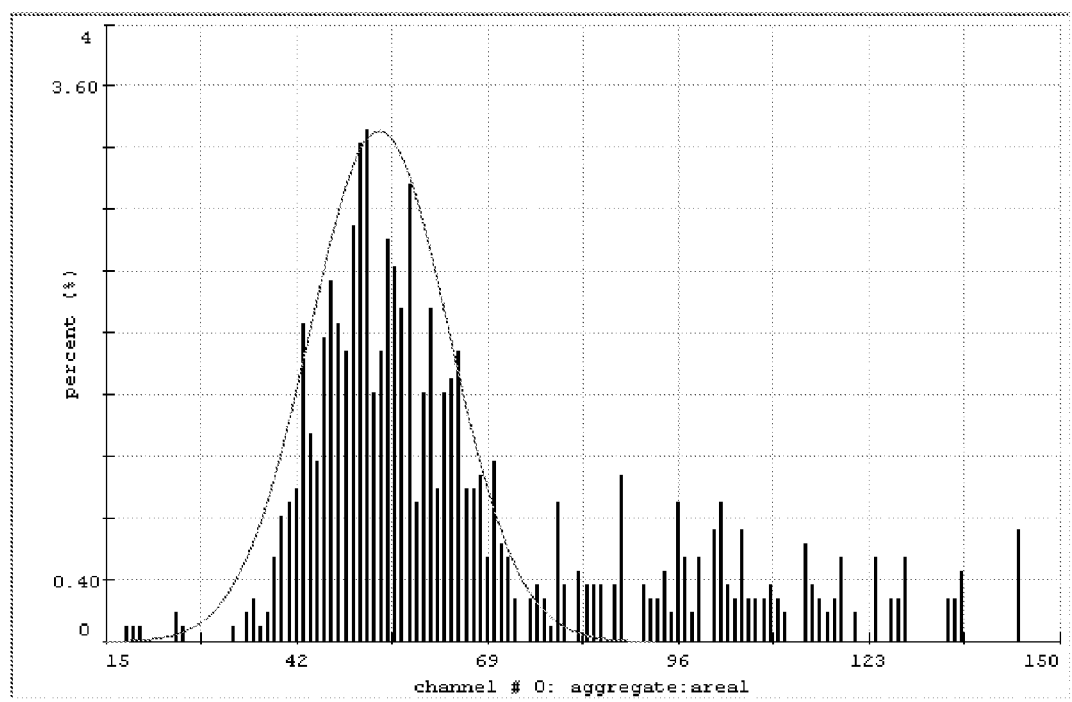
Figure 12:
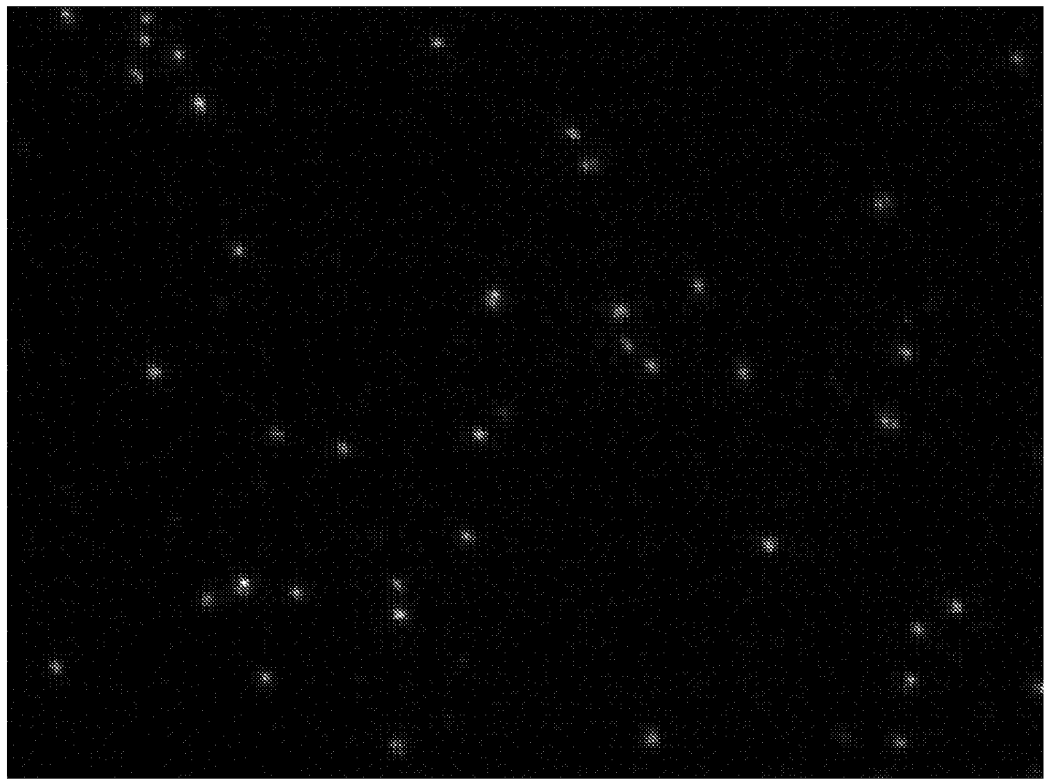
Figure 13:
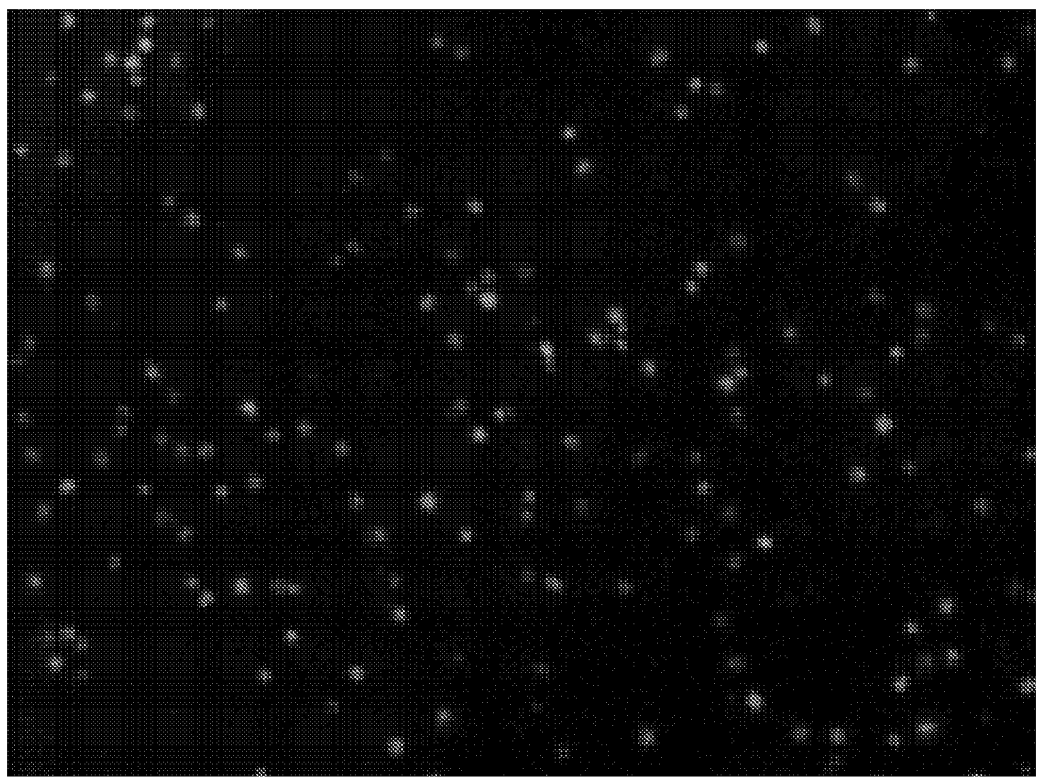
Figure 14:
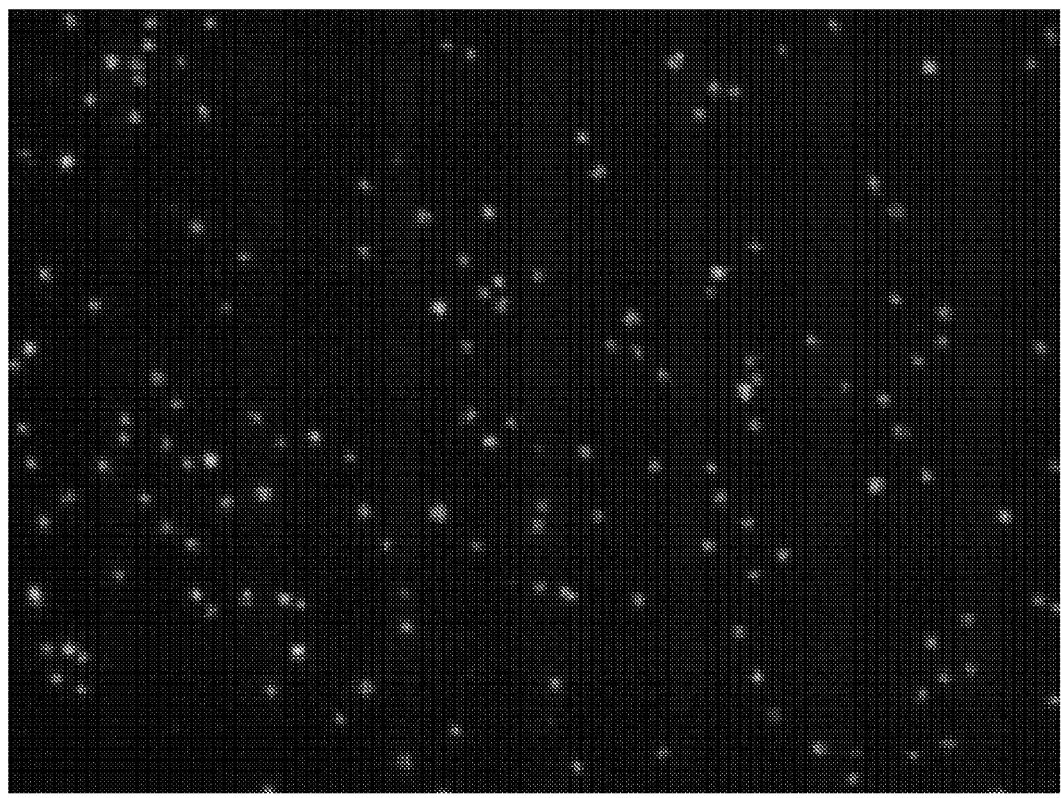
Figure 15:
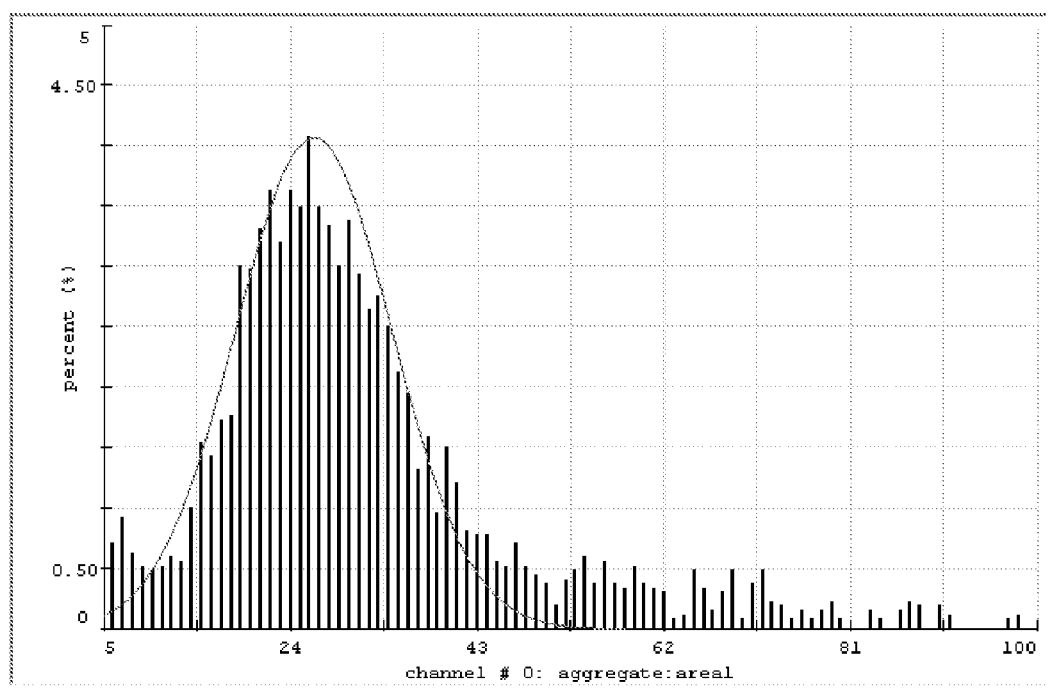
Figure 16:
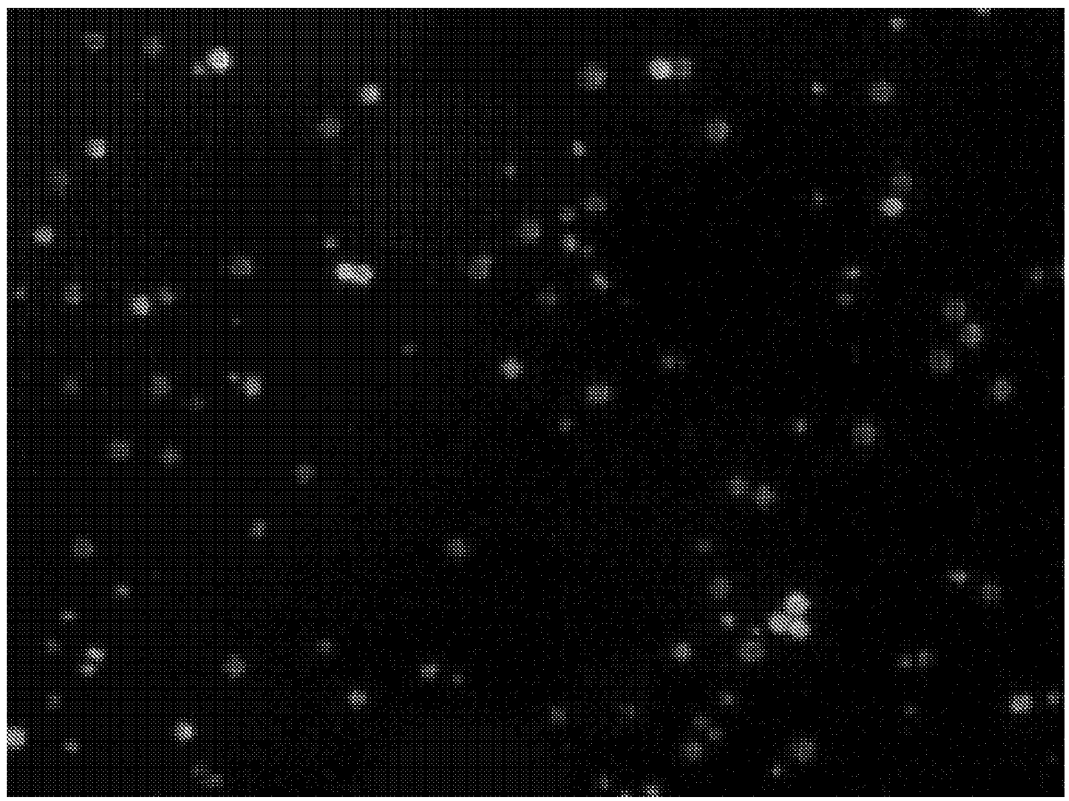
Figure 17:
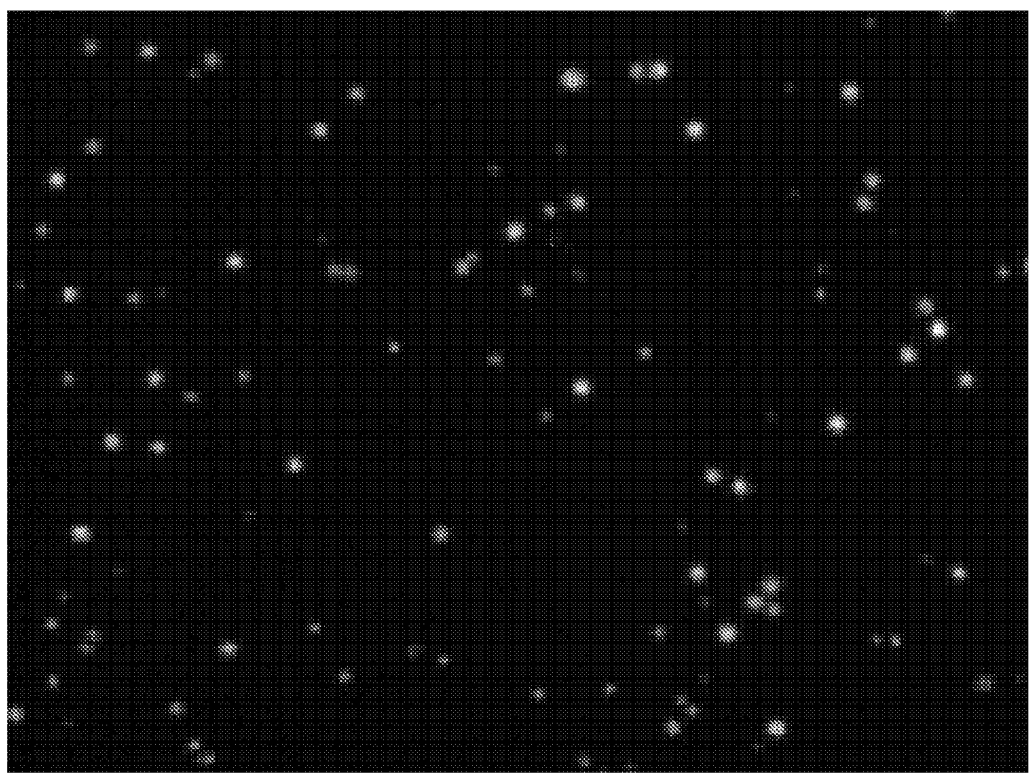
Figure 18:
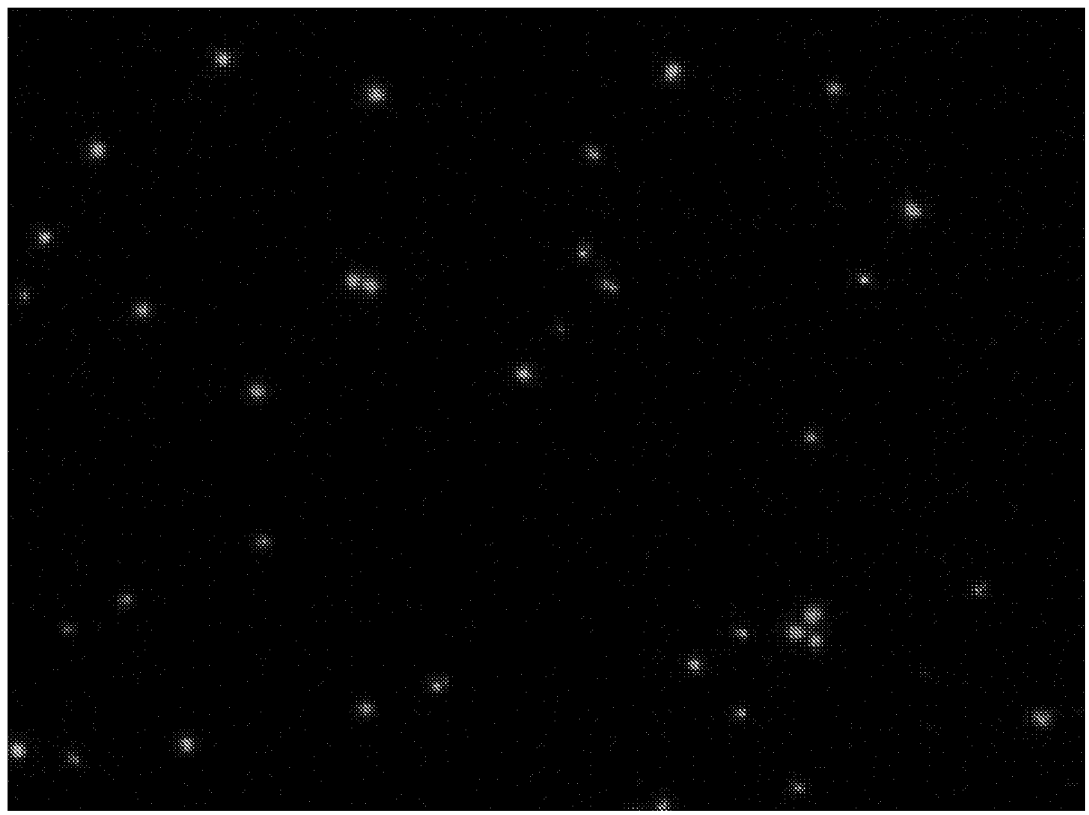
Figure 19:
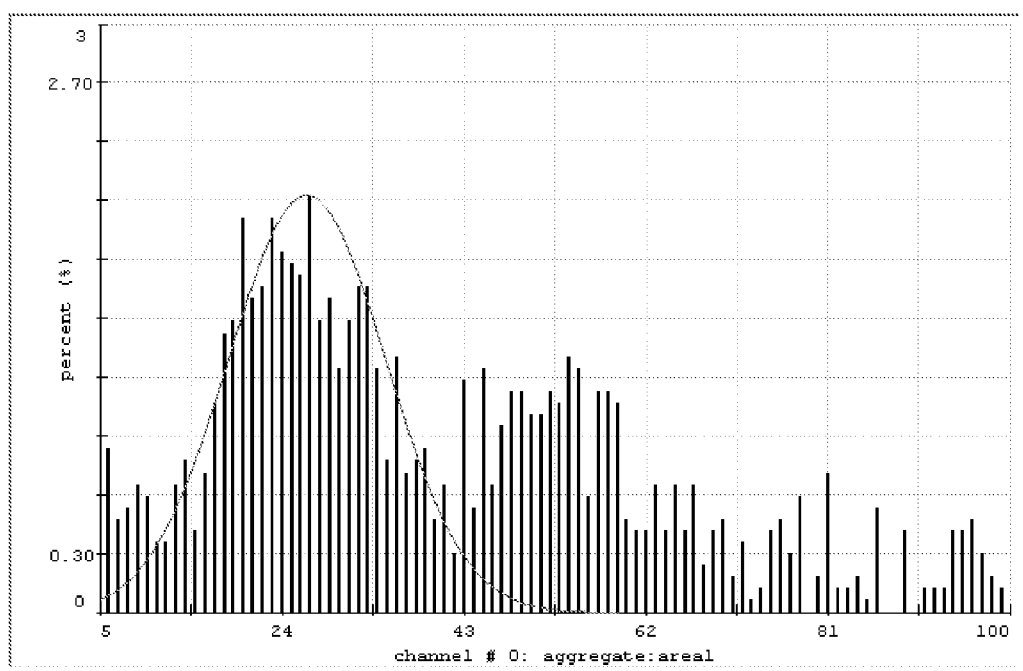
Figure 20:
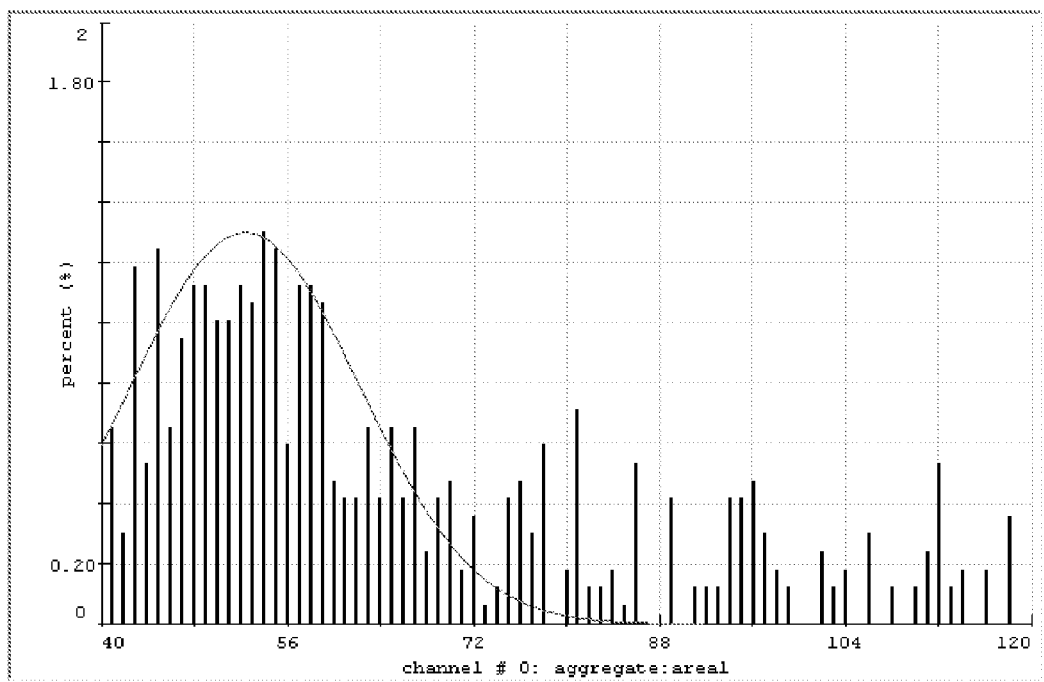
Figure 21:
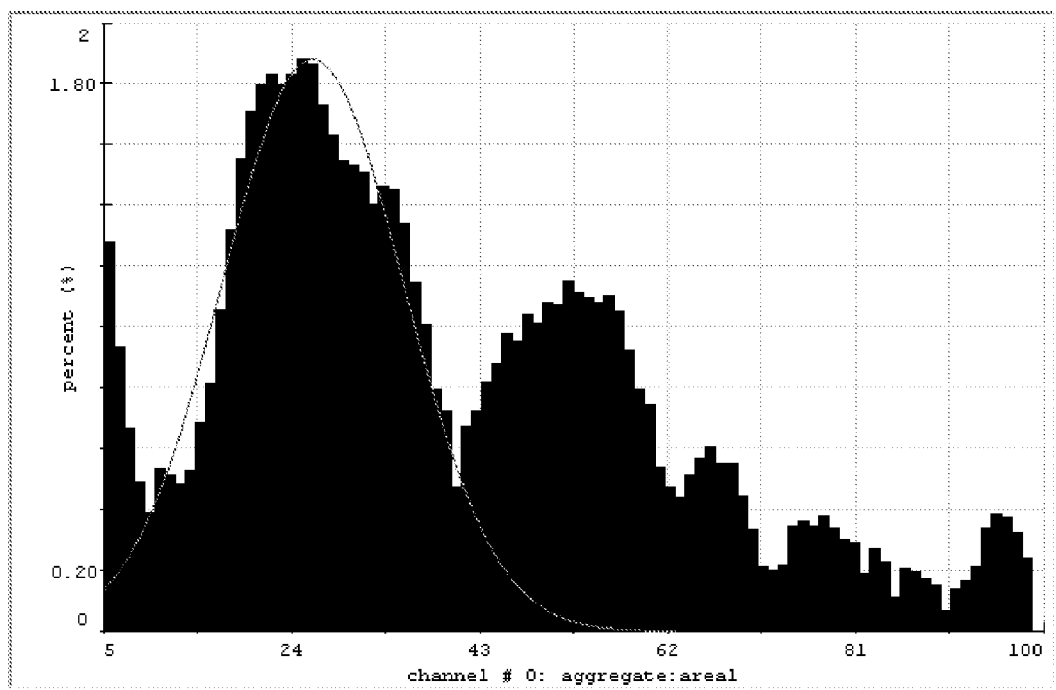

FIG. 1. Dark field imaging by dark field illumination.
FIG. 2. Dark field imaging system
FIG. 3. A compact dark field light source.
FIG. 4. An angled view of the dark field light source.
FIG. 5. The optical system of an cell analyzer apparatus.
FIG. 6, Dark field light source with polymer light guide.
FIG. 7. Angled and cross section view of the dark field light source with a polymer light guide.
FIG. 8-10. MCF7-cells, stained with DAPI and AO.
FIG. 11. Size histogram of MCF7 cells.
FIG. 12-14. A3 cells Jurkat, stained with DAPI and AO.
FIG. 15. Size histogram of A3 cells Jurkat.
FIG. 16-18. A3 cells Jurkat+MCF7-cells, stained with DAPI and AO.
FIG. 19-21. Size histogram of MCF7 and A3 cells mixed in suspension.

DETAILED DESCRIPTION OF THE INVENTION

Apparatus

An aspect of the invention relates to an apparatus for analysing a sample comprising particles such as cells and/or cell parts and wherein said analysis is performed at low magnification, the apparatus comprises
At least one dark field light source,
At least one other light source,
An image sensor for obtaining images of a sample, and
Magnifying means capable of projecting an image of the particles on the image sensor at a magnification below 10:1,
wherein light in said at least one dark field light source and said at least one other light source is obtained from LED and/or a laser diode.

It has surprisingly turned out that by using the apparatus or system as described herein it is possible to perform image analysis including at least one image obtained by dark field microscopy at a low magnification below 10:1. The contrast of the dark field images are high, hereby making it possible to perform image analysis by comparing images obtained by different techniques of the same section of a sample In the apparatus described above, the at least one other light source can be used in combination with a spectral filter resulting in a fluorescence image. Hereby the apparatus functions as a fluorescence microscope.

In an embodiment the apparatus comprises or is connected to a system capable of performing image analysis. Such a system may be a computer comprising a programme for image analysis.

The apparatus as described above may be combined with any features mentioned herein.

The at least one spectral filter may permit light of wavelengths between 200 and 1200 nm to pass through said at least one spectral filter. Preferably, the spectral filter is a long-pass filter, transmitting light above a certain wavelength. The excitation light is blocked, and the emitted fluorescence is transmitted through the spectral filter. Thus a spectral filter used with a light source emitting light in the range of e.g. 200-300 nm preferably is a spectral filter blocking light with a wavelength at and below 300 nm.

The spectral filter may permit passage of light in a interval of wavelengths, these intervals may selected from the group consisting of intervals of 410-450 nm, 415-525 nm, 450-500 nm, 500-555 nm, 520-595 nm, 555-605 nm, 595-750 nm, 630-1100 nm, and 660-1100 nm.

Preferably, the spectral filter is a glass substrate (e.g. BK7) with transmission from 320-1200 nm, or a fused silica substrate with transmission from 200-1200 nm.

By reference to FIG. 2, the following items are part of the imaging system: aperture (205), collimating lens (206), an optional spectral filter (207), aperture (208), focusing lens (209) or image sensor (210).

Also the apparatus may have a sample compartment which is suitable for keeping the sample stagnant at the time when images of the sample are obtained.

The apparatus or a computer connected to the apparatus may have the capability to pair images from different fluorescent or dark field channels, thus precisely identifying individual cells from image to image. The status of each cell is therefore measured by a multi-channel analysis.

Other features of the apparatus of which any one can be combined independently with one or more of the other features mentioned herein may be
Optics: Lens system with ×2 to ×10 magnification, ½" CCD with 1360×1024 pixels or more,
Sample device in the form of cassettes or disposable chamber slides (2, 4 and 8 chambers per slide),
Excitation (nm) e.g. one to nine LED light sources selected between light sources with peaks at 365, 405, 455, 475, 500, 525, 590, 630, 725 nm.
Emission (nm) e.g. one to ten interchangeable emission spectral filters selected between spectral filters permitting light with the following wavelengths to pass through: 410-450, 415-525, 450-500, 500-555, 520-595, 555-605, 595-750, 675-800, 630-1100, 660-

1100 nm, a glass substrate (BK7) with transmission from 320-1200 nm, and a fused silica substrate with transmission from 200-1200 nm.

Analysed volume may be 1-4 µl sample with the use of cassettes and 0.2-20 µl sample with the use of chamber slides, Optimal Range may be $5\times10^4$-$1\times10^7$ or even more particles/ml e.g. cells/ml, Cell types easily analysed by the apparatus can be mammalian cells, yeast, insect cells, and/or fish cells, A PC Platform may comprise Microsoft Windows 32 bit XP SP3, USB 2.0, Screen minimum 1024×768, recommended 2 GB RAM or another suitable system for performing the image analysis, Analysis time may typical by 15-60 seconds with 1 µl sample, Data presentation may be selected for one or more of images, tables, histograms, scatter plots, Weight of the apparatus may be 10-20 kg, e.g. about 14 kg, Dimensions of the apparatus may be 29×29×31 cm (H×W×D), Supply Voltage may be 100-240V~50-60 Hz and Power Consumption of 5/50 W (power save mode/peak).

In a preferred embodiment the image analysis of the apparatus is performed in respect of
at least two images obtained by dark field analysis or
at least one image obtained by dark field analysis and at least one image obtained by fluorescence analysis.

The number of images analysed in the image analysis may be any suitable, such as two dark field images and one fluorescence image; one dark field image and two fluorescence images; two dark field images and two fluorescence images, etc. Images to be analysed together are preferably obtained at similar magnification.

When two or more dark field images or two or more fluorescence images are analysed together, the images obtained by the same technique may be obtained with different wavelengths of the light emitted from the light source and/or with different wavelengths detected by detecting means of the image sensor.

In a preferred embodiment when utilising the apparatus the at least one image obtained by dark field analysis and the at least one image obtained by fluorescence analysis are paired in the image analysis system such that
particles such as cells and/or cell parts with at least one predetermined feature are identified in one of the techniques dark field or fluorescence, and
these identified particles such as cells and/or cell parts with at least one predetermined feature are discriminated when performing an image analysis of at least one image obtained with the other of the techniques dark field or fluorescence.

By "discriminated" is meant that particles are deleted, removed or eliminated from an image in the computer programme performing the image analysis. The number of particles used in the image analysis is hereby reduced.

Particles such as cells and/or cell parts which can be discriminated in an image analysis may be particles with a size below and/or above one or more predetermined sizes. With a determination of particles to be discriminated in an image obtained in one technique e.g. in dark field, these particles can be discriminated when analysing at least one image obtained in the other technique e.g. by fluorescence. In a preferred embodiment particles identified by dark field and which are to be discriminated can be removed in the analysis of at least one fluorescence image and thus only obtaining an analysis of the particles fulfilling certain criteria(s). In another preferred embodiment the particles to be discriminated are identified by fluorescence, and at least one dark field image is analysed with the identified particles discriminated.

In another preferred embodiment at least two images are used to identify particles to be discriminated and at least one image is used to analyse the particles not discriminated in the analysis. The at least two images used to identify particles to be discriminated may in a case where two images are used be two dark field images obtained at different dark field conditions, or it may be two fluorescence images obtained at different fluorescence conditions or it may be one dark field image and one fluorescence image.

Instead of identifying the particles to be discriminated, at least one image can be used to identify the particles to be used in a further analysis i.e. these particles fulfilling one or more positive requirements. Hereby the particles not identified to have the one or more positive requirements can be discriminated from the other images used in the analysis process. The use of number and order of dark field and fluorescence images as described above in respect of identification of particles to be discriminated i.e. identification based on negative features, can also be used when performing the identification of particles based on positive features.

The apparatus and method as described herein may comprise image analysis functions making it possible to identify particles such as cells and/or cell parts to be discriminated by the use of dark field analysis, hereby the particles which are identified are identified based on negative features i.e. the particles have one or more features which do not fulfil the requirement of the analysis to be performed. Similarly the identification of particles can be based on positive features i.e. one or more features which fulfil the requirement of the analysis to be performed.

The negative or positive features may be any feature connected to the purpose of the analysis performed. Such features may be connected to any of the features mentioned herein, e.g. the identification can be based on cell size (area, cross section, circumference), cell viability (viable or not viable), marker (marker or nor marker), morphological features of particles, cell membrane or cell wall integrity, and cell division progress.

The apparatus and method as described herein may be capable of identification of particles such as cells and/or cell parts to be discriminated, and where this identification is based on fluorescence analysis. The identification may be a negative or positive identification as described above in respect of dark field images. The discrimination of particles identified in fluorescence images can be performed in a similar manner as described in respect of discrimination of particles identified in dark field images.

The discrimination of particles whether based on negative and/or positive features and whether identified in dark field images and/or fluorescence images can be used to perform image analysis of particles. Examples of such analysis may be determination in respect of the number of particles; concentration of particles; size of the particles; size distribution of particles; morphological measurements of particles; cell membrane or cell wall integrity and/or cell division progress; viability of populations of cells and/or cell parts; frequency of particles carrying one or more specific markers; quantifying weak fluorescence signals of particles. In a preferred embodiment, particles are cells and/or cell parts. More preferred particles are cells.

In the apparatus described herein the at least one dark field light source may be located in a dark field light source unit and the at least one other light source may be located in another type of a light source unit. The dark field light source unit is a unit as herein described.

The apparatus may also comprise a light source rack for placement of at least two light source units e.g. including one or more dark field light source units, such as at least three light source units, e.g. at least four light source units, such as at least five light source units, e.g. at least six light source units, such as at least seven light source units, e.g. at least eight light source units. The light source rack of the apparatus may be a wheel or a carrousel.

The apparatus may further comprise a spectral filter or a spectral filter compartment located between the at least one dark field light source or the at least one other light source and said image sensor. Preferably the spectral filter is located between the sample compartment and the image sensor. More preferably the spectral filter is located between the sample compartment and a focusing lens.

The spectral filter of the apparatus may be located in a filter rack for placement of at least one filter, e.g. at least two filters, such as at least three filters, e.g. at least four filters, such as at least five filters, e.g. at least six filters, such as at least seven filters, e.g. at least eight filters. The filter rack of the apparatus may be a filter wheel.

The apparatus as described herein may have a numerical aperture of the imaging system which is below 0.1.

In a preferred embodiment the apparatus in the sample compartment is suitable for keeping the sample stagnant at the time when images of the sample are obtained. The number of images obtained as well as the image techniques used e.g. dark field and/or fluorescence may as described elsewhere herein.

Dark Field Light Source Unit

Another aspect of the invention relates to a dark field light source unit for use in microscopy with a magnification below 10:1, the light source unit comprising
- at least one light source for emitting light rays,
- at least one light guide for guiding the light rays emitted from the light source,
- at least one light directing device for deflecting light rays guided by the light guide,
- a blocking screen for blocking light rays emitted from the light source and for blocking light rays which is not guided by the light guide.

The dimensions of the dark field light source unit makes it suitable for use in a compact system for analyzing particles e.g. a system comprising a microscope and which can be connected to a image analyzing device such as a computer with image analyzing software. A compact system can be a system with dimensions of 25-35 cm of each side (height, width and depth). The compact system for analyzing particles can be a system such as the Nucleocounter NC-3000, and the compact system may thus have any features of the NC-3000 system, some of these features are mentioned herein.

Body of the Light Source Unit

The body of the light source unit with any of the features described herein preferably has a diameter between 20 and 50 mm, more preferably a diameter between 25 and 40 mm. Most preferably the diameter is about 30 mm. The height of the light source unit as described herein may have a height of between 20 and 50 mm, preferably of between 25 and 45 mm, more preferably of between 30 and 40 mm. most preferably of about 31 mm.

The body of the hollow reflecting light guide unit may be made of metal. This metal may be selected from the group of aluminium, stainless steel, titanium, nickel, copper or brass. When the body of the light guide unit is made of brass, the surface of the light guide can be chrome plated in order to have a high reflectance. Other choices of metals can also be surface treated in order to protect the surface against corrosion or to increase the reflectance.

The body of the hollow reflecting light guide unit may be made of polymer. The polymer parts can be made by injection molding, by machining or by another forming technique. The surface of the polymer parts should preferably be coated with a reflective layer, e.g. a metal layer as aluminium or a dielectric broadband reflective coating.

The body of the light guide unit may comprise a base part which is hollow with a conical hole, and into which a reflecting cone can be located to create a light guide. The three parts of the light guide unit: reflecting cone, diffuser and blocking screen can be held together by a screw joint in the center of the parts. The diffuser can have a hole in the middle, and it can thus be held in place by the pressure exerted by the joint between the blocking screen and the reflecting cone. The sub-assembly with the three parts can be glued in place in the part with the conical hole. The glue can be applied to the outer rim of the diffuser.

In an embodiment the distance from the light source (LED) to the sample device is 36.8 mm so as to fit exactly into a Nucleocounter NC-3000 system. The distance may vary from 10-50 mm, such as from 20-40 mm, for example 30-40 mm. Similarly, the diameter of the light source unit is preferably at the most 30 mm i diameter at the bottom part of the light source unit i.e. in the end where the light source is located, and preferably at the most 24 mm in the top of the light source i.e. in the part with the light blocking screen. In one embodiment the height of the light source unit is 30 mm at the edge and 31 mm in the center part of the light source unit.

Light Guide

The light source unit may have a light guide directing light away from a direct light path axis to avoid light passing directly from the light source towards the sample to be analysed.

The material of the light guide may be selected from the group of a hollow reflecting light guide, a polymer light guide, a glass light guide The light source unit may be surrounded by a material made of metal or of polymer.

The light guide made of polymer can be any polymer which is transparent in the wavelength range used. Preferred polymers are selected from the group of PMMA, COC (TOPAS), PC, PS, PE, PET.

The light source may have a light guide which guides the light rays from the light source in an angle of at least 5° measured from an axis from the position of the light source to a sample compartment. Hereby a light guide angle may be at least 5°, such as at least 10°, e.g. at least 15°, such as at least 20°, e.g. at least 30°, such as at least 40°, e.g. at least 50°.

In one embodiment, the center angle of the light guide is between 10 and 20°, such as between 12 and 18 degrees, for example between 14 and 16 degrees. In one particular embodiment, the center angle is 14.7 degrees.

The height of the light guide is preferably less than 30 mm where the height is measured along an axis from the position of the light source to a sample compartment which is illuminated by deflected light rays i.e. the measurement is performed along the direct light path axis.

In one particular embodiment the angle of the light going directly through the light guide and which is deflected by the light direction device at a radius of 9 mm is 17.7 degrees.

In this embodiment the angle of the reflecting cone is 16.3 degrees, and the angle of the reflecting conical hole is 13.3 degrees. Furthermore in this embodiment the width of the hollow reflecting waveguide is 3.8 mm at the bottom and 2.6 mm at the top, and the height of the light guide in this embodiment is 26.5 mm.

The construction of the light guide is such that the light rays emitted from the light source form the pointed part of a cone. The light source itself is the top of the cone and the light rays is directed from this point into a hollow cone shape until the light reaches the light directing device.

Incidence Angle

The light directing device of the light source unit deflects the light rays, this can be performed such that the light rays have an incidence angle selected between angles of about 5° to 80°. Preferred is an incidence angle of about 30° to 60°, More preferred is an incidence angle of about 40° to 60°, Yet further preferred is an incidence angle of about 50° to 60°, Most preferred is an incidence angle about 50°. The angle should be higher than the acceptance angle of the imaging optics, i.e. higher than 3.7 degrees when used in a Nucleocounter NC-3000 system. A preferred incidence angle is chosen based upon conditions of background and contrast in the image and the system into which the light directing device is fitted.

The incidence angle can also said to be at least of 5°, at least 10°, at least 15°, at least 20°, at least 25°, at least 30°, at least 35°, at least 40°, at least 45°, at least 50°, at least 55°, at least 60°, at least 70° or at least 80°.

The incidence angle can be determined by the diameter of the blocking screen as described elsewhere herein and the distance from the blocking screen to the sample area such that increasing the diameter of the blocking screen results in an increased incidence angle if the distance from the blocking screen to the sample area is not changed.

Blocking Screen

A blocking screen is used to block light passing directly from the light source towards the sample compartment. The form and dimension of the blocking screen may be any suitable such that the incidence angle of the light becomes the correct one and in a range as mentioned elsewhere herein.

The blocking screen can be located at any position between the light source and sample compartment such that an incidence angle as described elsewhere herein is obtained. Preferably the blocking screen is located perpendicular to the direct light path axis. Also preferably the blocking screen is located close to the light directing device. Most preferably the blocking screen is located close to the end of the light guide to determine the incidence angle of the deflected light.

In an embodiment the blocking screen is circular and located in a plane substantially parallel to the plane of a non-arched light source.

In the dark field light source unit the diameter of the blocking screen determines the incidence angle such that increasing the diameter of the blocking screen results in an increased incidence angle. The diameter of a circular blocking screen may be between 10 and 20 mm, between 20 and 30 mm, between 30 and 40 mm, between 40 and 50 mm. In a preferred embodiment the diameter of the blocking screen is between 10 and 20 mm. Further preferred is a diameter of the blocking screen of between 12 and 18 mm. Yet further preferred is a diameter of the blocking screen of between 14 and 17 mm. In one embodiment particularly adapted for the Nucleocounter NC-3000 system, the preferred diameter of the blocking screen is 16 mm.

When amending the diameter of the blocking screen it may also be necessary to amend the angle of the light guide, such that the light guide guides the light towards the end of the light guide i.e. towards light reflecting device e.g. towards the diffuser.

Light Source

The light source of the light source unit may be selected from the group of a light emitting diode (LED), a laser diode, a halogen light bulb, a Xenon light bulb, a Mercury light bulb or a incandescent Tungsten filament light bulb.

In an embodiment the light source is a wide spectral range device, such as a white LED, with a wavelength emission band of 400-700 nm.

In another embodiment the light source emits light in only a narrow wavelength band such as a single colour LED with peak wavelengths of e.g. 365, 405, 455, 475, 500, 525, 590, 630, 725, 785, 850, or 980 nm.

In another embodiment, the light source is a multi-colour device, such as a multi-colour LED emitter with individually addressable colour channels. In this embodiment, one or several wavelengths can be combined to form the spectral emission from the light source.

The light emitted from the light source may have a wavelength of between 200 and 1200 nm. Preferably the light source emits light with a wavelength between 300-400 nm, 400-500 nm, 500-600 nm, 600-700 nm, 700-800 nm, 800-900 nm or 900-1000 nm.

Light Directing Device

The light source unit according to any of the preceding claims, wherein the light directing device has a circular geometry in a plane substantially parallel to the plane of a non-arched light source.

The light directing device may be constructed such that it deflects light rays and such that the deflected light rays form the pointing part of a cone.

Different principles are possible for the function of a light directing device. With the use of a diffuser as a light directing device, the light is scattered by the material making up the light directing device. A light source unit with a diffuser is shown in FIG. 3. The diffuser can preferably be of the flashed white opal type, with a large angular intensity spread. However, the light directing device can also be a reflecting surface which reflects the light in the correct direction. The reflection may be an internal reflection as indicated in FIG. 6. The light directing device can also be a refractive lens, a Fresnel lens, a diffractive structure or a light guiding structure.

Dimensions of the Light Source Unit

The dark field light source unit as described herein is compact and may have a width of less than 50 mm. Preferably the light source has a width of less than 40 mm, more preferably of less than 30 mm.

The overall form of the light source unit may be in overall cylindrical. However, notches or attachments may be present on the light source unit e.g. as indicated in FIGS. 3 and 4.

Method for Analysing Particles

Another aspect of the invention relates to a method of analyzing a sample comprising particles such as cells and/or cell parts, the method comprising the steps of Obtaining a sample comprising at least one particle such as cells and/or cell parts, Obtaining at least one dark field image at a magnification below 10:1, Obtaining at least one fluorescence image at a similar magnification as used in respect of the at least one dark field image, Analyzing the at least one dark field image to obtain information in respect of the cells and/or cell parts of the sample, Analyzing the at least one fluorescence image to obtain information in respect of the cells and/or cell parts of the sample, Pairing information obtained from the dark field image and from the fluorescence image, and wherein the at least one dark field image and the at least one fluorescence image are obtained by the use of a LED and/or laser diode as a light source.

The pairing of information about individual cells and/or cell parts is made by an image analysis software in the instrument.

The method may further comprise image analysis of the at least one dark field image and of said at least one fluorescence image.

The image analysis may be performed in respect of at least two images obtained by dark field analysis or at least one image obtained by dark field analysis and at least one image obtained by fluorescence analysis.

The method may further comprise that the at least one image obtained by dark field analysis and at least one image obtained by fluorescence analysis are paired in the image analysis system such that particles such as cells and/or cell parts with at least one predetermined feature are identified in one of the techniques dark field or fluorescence, and these identified particles such as cells and/or cell parts with at least one predetermined feature are discriminated when performing an image analysis of at least one image obtained with the other of the techniques dark field or fluorescence.

The description in respect of discriminating particles, identification of particles as a negative and/or positive identification as described above in respect of the apparatus is also applicable in respect of the method. Also applicable is the combination of different images used in the image analysis.

In one preferred embodiment relating to the method, the particles such as cells and/or cell parts to be discriminated may be identified in dark field analysis. In another preferred embodiment of the method particles such as cells and/or cell parts to be discriminated are identified in fluorescence analysis.

In the method the at least one dark field image can be obtained by the use of a light source unit as described herein.

Other features described herein below in respect of a method may be combined with any of the features described above.

When obtaining images at low magnification e.g. 2:1, 4:1, 6:1, or 10:1 an increased number of cells is analysed in each image when compared to higher magnification of e.g. 100:1. The increased number of cells makes it possible to obtain images from a low number of sections e.g. only one section of the sample located in the sample compartment. The statistical significance of the measurement is thus increased due to the high number of cells in a single section of the sample.

In a preferred embodiment a high number of cells are analysed in each image, such as above 100 cells, e.g. above 200 cells, e.g. above 300 cells, e.g. above 400 cells.

In another embodiment, a sample to be analysed and which has a high number of cells, need not be diluted, as the sample when located in the sample compartment is analysed at a low magnification.

The method may be performed where two or more dark field images are obtained in respect of different wavelengths of the light rays and/or of different incident angles of the light rays.

The method may also be performed such that the two or more dark field images are obtained by consecutive use of two or more dark field light source units which emit light rays with different wavelengths, and where consecutive use means a change of dark field light source between obtaining the two or more dark field images.

In the method the two or more dark field images may be obtained by consecutive use of two or more dark field light source units which emit light rays with different incidence angles, and where consecutive use means a change of dark field light source between obtaining the two or more dark field images.

In the method the two or more dark field images may be obtained by consecutive use of two or more spectral filters for determining the wavelength of the light directed towards the image sensor, and where consecutive use means a change of spectral filter between obtaining the two or more dark field images.

In a preferred embodiment of analysis based on images obtained with two dark field images, the dark field images may be obtained at wavelengths far from each other e.g. at 360 nm and 725 nm.

The method may be performed at a linear magnification at or below 10:1, e.g. at or below 5:1, such as at or below 4:1, e.g. at or below 3:1, such as at or below 2:1.

When performing the method, the particles may be in a liquid sample. The sample may be a liquid sample comprising cells and/or cell parts. Any cells may be analyzed. The cells to be analysed may be dead or alive or the sample may comprise a mixture of dead and live cells optionally further comprising cell parts. Preferred is analysis of cells selected from the group of yeast, bacteria, and mammal cells. The cells may by nature be separated from each other, or if the cells normally are growing by having contact to each other, the cells may be separated from each other before performing the analysis as mentioned herein. Examination may also be performed of suspensions of cells such as yeast, bacteria, or cell and tissue fractions including cheek epithelial cells, chloroplasts, mitochondria, blood cells.

The method as described herein is based on pairing images from different fluorescent or dark field channels, hereby it is possible precisely to identify individual cells from image to image. The status of each cell can therefore be measured by a method based on a multi-channel analysis i.e. obtaining images of the same area of a sample by using different technique such as different excitation wavelength or different fluorescence method as described herein. The pairing is made by an image analysis software in the instrument.

The method as described herein may comprise determination of the number of particles such as cells and/or cell parts in a sample.

The method may also be used for determination of the concentration of particles such as concentration of cells and/or cell parts in a sample.

Furthermore, the method may be used for determination of the size of the particles such as for determination of the size of cells and/or cell parts in a sample.

In a preferred embodiment, the method is used for determination of the size distribution of particles such as determination of the size distribution of cells and/or cell parts in a sample.

It has turned out that the method can be used for morphological measurements of particles such as of cells and/or cell parts.

The method may comprise an additional step of obtaining at least one fluorescence image of the sample at a similar magnification as of the at least one dark field image, and wherein the at least one fluorescence image is used in the image analysis together with the at least one dark field image. Fluorescence image(s) can be obtained due to auto-fluorescence of the particles present in a sample. However the sample may also be stained with a dye before obtaining the at least one fluorescence image of a sample.

In a preferred embodiment a sample is stained with a dye capable of emitting fluorescent light. The dye may be a dye mentioned elsewhere herein. When performing image analysis of the sample at least one dark field image is obtained of a sample section and at least one fluorescence image obtained with one or more wavelength of the fluorescent light is obtained of the same sample section. The order of obtaining the dark field and fluorescence images may be any suitable e.g. first at least one dark field image followed by at least one fluorescence image. If obtaining images with two or more dark field light sources and with two or more fluorescence wavelengths, the order of obtaining the images may be any order, e.g. the images obtained may alternately be dark field and fluorescence images. The series of images may be initiated by obtaining a dark field image. If the fluorescent signal is weak, and photobleaching of the dye may be a concern, the series of images may be initiated by obtaining a fluorescent image.

The method image analysis of the at least one dark field image and the at least one fluorescence image obtained as described herein is used for determination of any of the features of particles such as of cells and/or cell parts. The features may be selected from the group of
  number of particles such as of cells and/or cell parts,
  concentration of particles such as cells and/or cell parts,
  size of the particles such as of cells and/or cell parts,
  size distribution of particles such as cells and/or cell parts,
  morphological measurements of particles such as of cells and/or cell parts,
  cell membrane or cell wall integrity and/or cell division progress,
  viability of populations of cells and/or cell parts,
  frequency of particles such as of cells and/or cell parts carrying a specific marker,
  quantifying weak fluorescence signals of particles such as of cells and/or cell parts.

The dark field images obtained as described elsewhere herein can be used in combination with fluorescence images to analyze e.g. cell concentration (counting), cell size and size distribution and cellular markers. An advantage of the described technique is that it can be used in a low magnification system to image small objects, and optionally in combination with fluorescence images that can reveal other features of the cells. It has been demonstrated that a high image contrast can be achieved with the method described herein.

Samples

The method according to the invention may be used for analysis of any sample including a biological sample.

Preferably the sample is selected from a body fluid sample, a tissue sample, a fermentation sample, a liquid cultivation sample, a cell culture sample, a water sample, a beverage sample, a pharmaceutical sample, a microelectronic product.

Preferred samples also include a sample selected from a blood sample, a urine sample, a saliva sample, a semen sample, a solubilised tissue sample, a milk sample, a faeces sample, a tear sample.

A biological sample may be obtained from a sample selected from a liver sample, a kidney sample, a muscle sample, a brain sample, a lung sample, a skin sample, a thymus sample, a spleen sample, a gastrointestinal tract sample, a pancreas sample, a thyroid gland sample.

Biological samples may originate from a human sample, a mouse sample, a rat sample, a monkey sample, a dog sample. However, the invention also relates to analysis of material selected from a bacterial culture, a mammalian cell culture, a protozoa culture or other cell cultures.

Dark Field Principle

Dark field microscopy imaging is an arrangement where the direct light path of the illumination light is blocked in the system. Only light that is scattered or diffracted from physical objects is transmitted. The technique gives a high contrast image, and is very useful for small objects with a refractive index close to that of the surrounding media.

One embodiment which has been tested in the NC-3000 instrument is through the use of dark field illumination (see FIG. 1). The incidence angle of the illumination light is higher than the acceptance angle of the imaging system. This technique is especially useful in a low numerical aperture system as the NC-3000.

The numerical aperture is defined as:

$$NA = n \cdot \sin \Theta_{max}$$

$\theta_{max}$ is the angle of incidence of the marginal ray of the system, i.e. the ray with the largest angle that is accepted. The parameter n is the refractive index of the medium surrounding the lens (1.0 for air). The numerical aperture of the imaging system in the NC-3000 is 0.065, giving a maximum acceptance angle of 3.7 degrees (half angle).

The Dark Field Configuration

A full system showing the parts involved in the dark field imaging of cells is shown in FIG. 2.

The light source (201) can be a suitable compact light source such as a light emitting diode (LED), a laser diode, a halogen light bulb, a Xenon light bulb, a Mercury light bulb or a incandescent Tungsten filament light bulb. In one embodiment, the light source is a wide spectral range device, such as a white LED. In another embodiment, the light source emits light in only a narrow wavelength band such as a single colour LED. The wavelength of the emitted light can be in the ultraviolet range of the spectrum, the visible range or in the near infrared range. A preferred range for the emitted wavelength is between 200-1200 nm when consideration is taken to the transparency of optical materials and sensitivity of available image sensors such as CCD cameras, CMOS cameras, quantum dots, scanned linear arrays, image intensified devices etc. In the embodiment shown in FIG. 2, the emitted light should have a broad angular distribution in order to illuminate the light directing device (203).

The center part of the emitted light from the light source (201) will be blocked by the blocking screen (202). This screen should preferably be circular in shape, and be made from a material that completely blocks the light, e.g. a metal. Part of the emitted light will pass through the light directing device (203), where it will be deflected into the suitable dark field at an illumination angle of, e.g. 50 degrees. The light directing device can be a light diffuser, a positive lens, a mirror, a Fresnel type positive lens, a prism, a light guide or a diffractive device. The device should be able to redirect the light coming in with any angle to an angle of +50 degrees. The distribution of light in the sample area should be uniform, which is achieved by having a circular geometry in the light directing device.

The sample compartment (204) is an enclosed device consisting of a bottom layer and a cover layer. The material can be glass or a polymer. The thickness of the sample compartment is well defined, thus giving a controlled measurement volume. A background reducing aperture (205) ensures that only light having the correct directionality enters the imaging part of the optics. The imaging part consists of a collimating lens (206), an optional spectral filter (207), an aperture (208), a focusing lens (209) and finally the image sensor (CCD camera) (210). In the embodiment with white light for the analysis, there is no spectral filtering function in the filter substrate, as e.g. a pure glass substrate (207). In other embodiments, the spectral filter (207) ensures that only a certain wavelength band of the scattered light is detected by the image sensor. By having several spectral filters in the instrument, e.g. in a filter wheel as in the NC-3000, the light scattering dependence on wavelength can be measured. This feature can also be used to find the optimum spectral conditions with regards to contrast in each measurement.

The aperture (208) is the limiting aperture of the system, and ensures a sufficient depth of focus. The final parts of the optical system are the focusing lens 209, which focuses the light onto the CCD-chip of the camera (210).

Example of a Dark Field Light Source

A dark field light source that has been realized and tested in the NC-3000 is shown in FIG. 3. The light emitting device (301) is in this case an LED with a spherical lens. The light is emitted from the LED in a wide angular distribution of more than 35 degrees half angle. The hollow reflecting light guide (302) consists of two metallic parts, one with conical hole, and the other with the shape of a cone. The light guide directs the light to the outer parts of the light diffuser (303) where the light is scattered in all directions. A blocking screen (304) stops any internally scattered light in the diffuser and precisely defines the light emitting area on top of the diffuser.

Combination of Fluorescence and Dark Field Image Analysis

A clear advantage in the cell analysis is to perform combined measurements of the emitted fluorescence from cells as well as scattered light from the cells. The same sample can be imaged in one or several fluorescence channels, each channel expressing a particular feature of the cells, e.g. viability, vitality, cell cycle etc. The dark field measurement can be used to independently measure the concentration of cells, giving a total cell count.

One clear advantage of the method as described herein is for the cell size determination. This is difficult to achieve by fluorescence imaging as the apparent size will vary according to distribution of fluorophores in the cell, and the amount of fluorophores. The light scattering of the cell mainly takes place off the cell periphery, which is why the dark field technique is very suitable for measuring the size of the cells. Size assessment by the dark field image does not rely on staining or the incorporation of fluorophores in the cell, which makes it a robust and reproducible method. It is possible to precisely identify each cell in the fluorescence and dark field images, and hereby extract multichannel information on each individual cell. This makes it possible to isolate populations within the sample with a specific feature.

It is also possible to use a combination of the two methods fluorescence and dark field to obtain a more specific analysis of only one parameter, e.g. total cell concentration due to the combination of two different principles of analysis.

If several parameters are to be measured in the same assay, the use of dark field for one or several parameters can reduce the number of fluorescence channels needed, thus reducing the complexity of the incorporation chemistry, incubation time etc. The effects of fluorescence quenching can also be reduced or avoided through the use of dark field analysis.

Analysis without Chemical Modification

Another advantage of the dark field imaging technique is that it does not require any chemical modification of the sample. In certain cell assays it is undesirable to use cell staining or fluorophore incorporation as this may have an impact on the cell viability and growth. Any problems due to bleaching of the fluorophore or increased background due to free fluorophore in the surrounding media are also avoided.

There are several other advantages with a non-chemical analysis method. These include environmental issues and ease of disposal of the sample as it will not contain possibly toxic fluorophore substances. The cost per analysis and time per analysis can also be lowered without chemical staining.

Mixed Sample Analysis

Samples having multiple types of particulates can be analyzed with a combination of fluorescence and dark field imaging. Particulates that do not have a cell nucleus, such as red blood cells, or a simple cell organism such as bacteria may be analyzed with the dark field technique. Other particulates in the same sample can be analyzed with fluorescence, thus giving a total measurement of the sample.

Spectrally Dependent Scatter Analysis

As mentioned in the descriptive part above, it is possible to obtain dark field images of several wavelength channels. In practice this can be achieved by either having a broadband light source such as a white LED and then filtering out the scattered light in different spectral channels, or by having different light sources, each of which emitting a specific wavelength. The information of the obtained spectral channel images can be used to extract spectrally dependent information and to increase the accuracy of e.g. a cell size measurement. Due to the nature of the cells and the cell matter, it is likely that there will be a difference in refractive index contrast between the cell and the surrounding media dependent on wavelength. This means that the intensity and angular distribution of the scattered light will vary with wavelength. It is possible to use this information to calibrate a very accurate cell size measurement.

Measurement without Bleaching of Fluorophores

In a combined measurement with fluorescence and dark field analysis, there is a possibility to completely avoid fluorescence bleaching of the fluorophores during the dark field measurements. This can be beneficial in some cases where the fluorescence signals are weak, and irreversible photodestruction of the fluorophores can occur. If the wavelength of the dark field source is chosen to be outside of the excitation spectra of all used fluorophores, bleaching phenomena are avoided. There is a large number of available fluorophores with excitation wavelengths between 200-700 nm. Choosing a dark field light source with a wavelength above 700 nm will eliminate bleaching of the fluorophores.

Angular Dependent Scatter Analysis

It is possible to perform angular dependent scatter analysis by use of the dark field technique in the system of the invention. This can be achieved by designating individual dark field light sources, each having a particular illumination angle on the sample area, e.g. 50 degrees, 40 degrees, 30 degrees. This can easily be accomplished in practice by changing the diameter of the blocking screen and the hollow light guide as illustrated before. Dark field images can then be obtained of the same sample with different angular illuminations. As with the spectrally dependent analysis mentioned above, the angular dependent scatter information can be used to ascertain cell size with high accuracy. Other aspects of cell morphology can most certainly also be obtained from this information.

Morphology Measurement of Cells

Since the dark field imaging technique is essentially an imaging technique giving a representation of the cells physical structure, it can also be used to extract morphological information about the cells. For cells having a certain size, this can be performed in a low magnification system. Examples of morphological data that can be extracted are cell membrane or cell wall integrity and cell division progress.

Examples of Applications of the Methods

Using Dark Field Image Analysis for Counting of Total Cells

Dark field image analysis can be used for identifying and counting total cells in a sample without dye staining. Sample can be tissues, cell lines and primary cells and may be obtained from blood, semen, milk, bioreactors, T-flasks, growth plates.

Combination of Dark Field and Fluorescence Imaging can be Used for Determining the Viability of Cell Populations Sample is stained with a cell impermeable fluorescent dye, such as DAPI and propidium iodide. Only dead cells with compromised cell membranes will be stained. Dead cells can be detected by excitation of the cell impermeable dye (UV/V light in case of DAPI) and collecting the emitted light (blue light in case of DAPI). The number of total cells in the stained population is determined using dark field imaging. Having information about total and dead cells the viability is calculated as:

$$\text{Viability} = \frac{\text{Concentration of total cells} - \text{Concentration of dead cells}}{\text{Concentration of total cells}} \times 100\%$$

Combination of Dark Field and Fluorescence Imaging can be Used for Determining Frequency of Cells Carrying a Specific Marker Sample is stained with a fluorochrome that labels a specific cellular marker. This can be e.g. an fluorochrome-conjugated antibody that interacts with a specific antigen, such as a Cluster of Differentiation (CD) marker. Cells expressing the specific marker is detected by fluorescence imaging, whereas the number of total cells in the examined population is determined using dark field imaging. Having information about total and labeled cells the frequency of cells positive for the specific marker is given as:

$$\text{Frequency of positive cells} = \frac{\text{Concentration of labeled cells}}{\text{Concentration of total cells}}$$

Sample may also be stained with several flurochromes labeling different cellular markers.

Combination of Dark Field and Fluorescence Imaging can be Used for Quantifying Weak Fluorescence Signal.

The sample is stained with a fluorochrome that labels a specific cellular marker. Using dark field imaging, cells in the population are identified. Next, light emitted by the labeled marker is detected using fluorescence imaging and the two images are superimposed by digital image processing. The dark field image is used for identification of the cells and for determining their size. Based on this information the fluorescence is quantified by integrating signal intensity over the cell area.

Thus, the position and optionally size of at least one particle are identified in a dark-field image, and the position and optionally size may be used to quantify the level of fluorescent signal in the fluorescent image, where said particle is located. By knowing the exact position and size of the particle in the image, the analysis can be restricted to this particular area and the level of fluorescence can be quantified even though it is only a few percent over the background signal.

Using Dark Field Image Analysis for Determining Cell Motility

The dark field image can be used to identify single mobile cells, e.g. sperm cells. By tracking the individual cells through consecutive images taken of the sample, the individual cell motility and directionality, as well as the overall degree of motility and directionality in the sample can be determined. The dark field image can be combined with a fluorescent image to also determine other features of the cells, such as membrane integrity.

Using Dark Field Image Analysis for Determining Cell Size Distribution

Light emitted from the dark field light source is mainly scattered by the cell membrane (plasma membrane). That is to say that the area of scattered light reflects the area of the cell. Thus, dark field imaging may provide precise information about cell sizes in a population. This information can be used for discriminating between different cell types in a mixed population, such as lymphocytes, neutrophils, basophils and erythrocytes in a blood sample, or it can be used for measuring cell status, such as viability, vitality and proliferation rate.

The method as described herein will also be of interest to those working in areas such as stem-cell research, cell counting and viability, apoptosis and cancer, vaccine production, gene expression and transfection and cell-cycle studies.

An important feature of the method when performed in the apparatus as described herein is its fast analysis time which enables a complete analysis such as a viability assay to be performed within 2 min, including sample handling.

Benefits of the method and the apparatus as described herein e.g. when performing the method with the Nucleocounter NC-3000 include: high precision and reproducibility; fast analysis (very short total operation time); automated data analysis and superior data-visualisation software; calibration, maintenance and service free; all-in-one instrument with a small footprint; and plug and play system. Image analysis, calculations and data reporting can be performed automatically assuring superior and standardized results even with different users.

DETAILED DESCRIPTION OF THE DRAWINGS

FIG. 1, Dark field imaging by dark field illumination. Light (102) emitted from a light source (not shown) is deflected. A blocking screen (101) secures that no light is directed from the light source and directly towards the specimen (particle (103)). The illumination light (102) is scattered or diffracted by the particle (103). Scattered or diffracted light (104) can reach an imaging lens (105) and an image of the sample comprising particles (103) is possible.

FIG. 2. Dark field imaging system suitable to obtain images of samples, this system could be compressed as in the NucleoCounter® NC-3000™. Light is emitted from a dark field light source (201) and directed towards a light directing device (203) by a light guide (not indicated except for the direction of the emitted light). A blocking screen (202) secures that no light is directed directly from the light source and towards the sample compartment (204). Light deflected by the light directing device (203) is directed towards the sample compartment (204) where the illumination light is scattered or diffracted by the particle as shown in FIG. 1. A part of the scattered and diffracted light passes an aperture (205). The light is then led through a collimating lens (206) optionally through a spectral filter (207), a second aperture (208) and a focusing lens (209) and towards an image sensor (210) where an image of the sample is obtained. The image can be analyzed by image analyzing means in a computer.

FIG. 3. A compact dark field light source. The dark field light source unit comprises a light source, which is illustrated by a light emitting device (LED) (301). Light emitted by the light source is directed through the light guide, which in this embodiment is a hollow reflecting light guide (302). The light is deflected by a light diffuser (303), and a light blocking screen (304) secures that no light is transmitted directly from the light source to the sample.

FIG. 4. An angled view of the dark field light source unit as shown in FIG. 3.

FIG. 5. An example of a compact optical system is shown. The imaging system as shown in FIG. 2 is used in this optical system. The system may be a cell analysis system. The cell analysis system is based on a multitude of individual light sources (502), which e.g. can be dark field light sources, bright field light sources, fluorescence light sources. There may be one light source for each fluorescent channel, and one light source for white light dark field illumination. Optionally, there can also be dark field sources with single wavelength bands. The light sources are mounted on a rotating wheel (501). When a sample is analyzed, images are usually taken in the relevant fluorescent channels as well as the dark field channel. This is accomplished by rotating the light source wheel (501) to place the light source under the sample position illustrated by the sample compartment (503). The rotating filter wheel (506) is correspondingly placed with the correct spectral filter in the light beam path. For the dark field image with white light, a clear glass window is used instead of a spectral filter in the rotating filter wheel (506). Also an aperture (504), collimating lens (505), focusing lens and aperture (507 and an image sensor (508) is shown in the Figure. Obtained images of a sample can be analyzed with image analyzing means in a computer. The light source wheel as well as the filter wheel makes it easy to obtain images of the same section of the sample in the sample compartment (503), which is important for the image analysis.

FIG. 6. The Figure shows an embodiment of a dark field light source with polymer light guide. The light (602) is emitted from the LED with lens (601). The light enters the polymer light guide (603) and is directed towards the surface for reflection (604) where the light is reflected by total internal reflection. After reflection, the light exits the light guide, and illuminates the sample area (606). The blocking screen (605) ensures that there is no light that is directly transmitted from the LED to the sample area. The polymer light guide may be integrated into the dark field light source of FIGS. 3 and 4 and used as described e.g. in respect of FIGS. 2 and 5.

FIG. 7. Angled and cross section view of the dark field light source with a polymer light guide as shown in FIG. 6.

FIG. 8. The image shows MCF-7-cells (breast cancer cells), stained with DAPI (4',6-diamidino-2-phenylindole) and AO (Acridine Orange). The DAPI dye is able to pass through the cell membrane and bind to the DNA. It will however pass the cell membrane much less efficiently in live cells, why the staining is strongest in dead cells. The cells are imaged in the NC-3000 instrument with a fluorescent channel 1A (360 nm) that excites DAPI in dead cells. The fluorescent light is filtered by an emission filter with a center wavelength of 470 nm (415-525 nm). The spectral window of this filter corresponds to the emission peak of the DAPI dye. The figure shows a sub-part (1/16) of the total image. The exposure time was 83 ms. The total cell count in the image, corresponding to dead cells in the sample is 2. The cell count was obtained with manual counting from the image.

FIG. 9. The image shows MCF-7-cells, stained with DAPI and AO. This is the same sample as shown in FIG. 8, and the figure shows the same sub-part of the total image. The sample was imaged with a fluorescent channel 3 (475 nm) that excites AO in all cells. The fluorescent light is filtered by an emission filter with a center wavelength of 558 nm (520-595 nm). The spectral window of this filter corresponds to the emission peak of the AO dye. The exposure time was 34 ms. The total cell count in the image is 63 cells+2 weak. The cell count was obtained with manual counting from the image. The two weak cells are the two dead cells as identified by the DAPI measurement of FIG. 8. The arrows indicate the two cells seen in FIG. 8.

FIG. 10. MCF-7-cells, stained with DAPI and AO. This is the same sample as shown in FIGS. 8 and 9. The sample was imaged with a dark field channel (white LED 400-700 nm) (dark field light source) that shows all cells. The exposure time was 600 ms. The total cell count in the image is 65 cells. The cell count was obtained with manual counting from the image. The thin arrows indicate dead cells as identified by the DAPI measurement and identified in FIG. 8. The dead cells show some indication of a morphology difference to the living cells. The thick arrow points to a cell that is possibly going through cell division.

FIG. 11. The figure shows a size histogram of the MCF-7 cells as shown in FIG. 8-10. The measurement was done on the full image by an automated image analysis method in the NC-3000 instrument. The image analyzed was a dark field measurement as in FIG. 10, showing all cells. The average size of the cells are 53.6 pixels. The size unit of pixels is used in order to compare the size of different cells in this experiment. After calibration, the pixel size can be transformed to a physical unit, e.g. $\mu m^2$.

FIG. 12. The image shows A3 Jurkat cells (T lymphocyte cells), stained with DAPI and AO. The cells are imaged in the NC-3000 instrument with a fluorescent channel 1A (360 nm) that excites DAPI in dead cells. The figure shows a sub-part (1/16) of the total image.

FIG. 13. The image shows A3 Jurkat cells, stained with DAPI and AO. This is the same sample as shown in FIG. 12. The sample was imaged with a dark field channel (white LED 400-700 nm) (dark field light source) that shows all cells. The figure shows a sub-part (1/16) of the total image.

FIG. 14. The image shows A3 Jurkat cells, stained with DAPI and AO. This is the same sample as shown in FIGS. 12 and 13. The sample was imaged with a fluorescent channel 3 (475 nm) that excites AO in all cells.

FIG. 15. The figure shows a size histogram of the A3 Jurkat cells sample shown in FIG. 12-14. The measurement was done on the full image by an automated image analysis method in the NC-3000 instrument. The image analyzed was a dark field measurement as in FIG. 13, showing all cells. The average size of the cells are 26.3 pixels.

FIG. 16. The image shows a mixture of A3 Jurkat cells+ MCF-7 cells, stained with DAPI and AO. The sample was imaged with a dark field channel (white LED 400-700 nm) (dark field light source) that shows all cells. The figure shows a sub-part (1/16) of the total image.

FIG. 17. The image shows a mixture of A3 Jurkat cells+ MCF-7 cells, stained with DAPI and AO. This is the same sample as shown in FIG. 16. The sample was imaged with a fluorescent channel 3 (475 nm) that excites AO in all cells.

FIG. 18. The image shows a mixture of A3 Jurkat cells+ MCF-7 cells, stained with DAPI and AO. This is the same sample as shown in FIGS. 16 and 17. The cells are imaged in the NC-3000 instrument with a fluorescent channel 1A (360 nm) that excites DAPI in dead cells.

FIG. 19. The figure shows a size histogram of MCF-7 and A3 Jurkat cells mixed in suspension. This is the same sample as shown in FIG. 16-18. The measurement was done on the full image by an automated image analysis method in the NC-3000 instrument. The image analyzed was a dark field measurement as in FIG. 16, showing all cells. The average size of the A3 Jurkat cell population is 26.5 pixels and of the MCF-7 cell population is 52.3 pixels.

FIG. 20. The figure shows the size histogram of MCF-7 cells and A3 Jurkat cells mixed in suspension. This is the same sample as shown in FIG. 16-18, and the same histogram data as in FIG. 19. The histogram in FIG. 20 is with smoothing of the data.

FIG. 21. Size histogram of MCF7 and A3 cells mixed in suspension. Smoothing of data. Dark field image. Average size of the A3 cell population is 26.5 pixels and of the MCF7 cell population is 52.3 pixels.

EXAMPLES

Example 1

Combination of Dark Field and Fluorescence Imaging at Low Magnification can be Used for Determining the Viability of Cell Populations Materials and Methods. MCF-7 (ATTC HTB-22) and Jurkat (A3, ATCC-CRL-2570) cells were cultivated at 37° C. in a humidified air atmosphere with 5% $CO_2$ in RPMI (Invitrogen, #61870)+10% FCS (Invitrogen, #10108-165) in T25 flasks. Jurkat cells were harvested at a density of $3.5 \times 10^6$ cells/ml. MCF-7 cells were harvested at 75% confluency with 0.5 ml of trypsin (Invitrogen, #25300) and diluted to a density of $1.7 \times 10^6$ cells/ml with medium (RPMI+10% FCS). The two cell lines were stained with 1 µg/ml DAPI (4,6-diamino-2-phenylndole, Invitrogen, #D1306) and 1 µg/ml AO (Acridine Orange, SigmaAldrich, #A-6014) prior to mounting on a microscope slide. Cells were imaged at 2 times magnification using a NucleoCounter NC-3000 (Chemometec). DAPI stained cells (dead cells) were detected by exciting the fluorochrome at 365 nm and collecting the emitted blue light (415-525 nm). AO stained cells (total cells) were detected by exciting the fluorochrome at 475 nm and collecting the emitted green light (520-595 nm). The AO and DAPI stained samples were furthermore imaged with a dark field channel (white LED, 400-700 nm) to identify all cells in the populations.

Results.

AO enters both dead and living cells and, hence, stains the total cell population. In contrast, DAPI is membrane impermeant and thus excluded from viable cells. Double staining with AO and DAPI can therefore be used to determine the viability of cell populations (WO 2010/006615). Here it demonstrated that dark field imaging at low magnification (2:1) can be used to identify the total cell population of the cell lines, MCF-7 and Jurkat. As shown in FIGS. 9, 10, 13 and 14 dark field imaging of AO stained cells mimics the images produced by measuring the green fluorescence from AO. Hence, the same cells are identified using dark fields imaging and fluorescence imaging of AO stained cells.

Moreover, this example demonstrates that the combination of dark field and fluorescent imaging of DAPI stained cells can be used for determining the viability of cell populations. FIGS. 8 and 12 show dead DAPI stained MCF-7 and Jurkat cells, respectively. Combined with the information from dark field imaging of the same cells, FIGS. 10 and 13, the number of total and dead cells can estimated and, thus, the viability can be calculated.

Example 2

Dark Field Imaging can be Used for Estimating Size Distributions of Cells

Materials and Methods. MCF-7 (ATTC HTB-22) and Jurkat (A3, ATCC-CRL-2570) cells were cultivated at 37° C. in a humidified air atmosphere with 5% $CO_2$ in RPMI (Invitrogen, #61870)+10% FCS (Invitrogen, #10108-165) in T25 flasks. Jurkat cells were harvested at a density of $3.5 \times 10^6$ cells/ml. MCF-7 cells were harvested at 75% confluency with 0.5 ml of trypsin (Invitrogen, #25300) and diluted to a density of $1.7 \times 10^6$ cells/ml with medium (RPMI+10% FCS). The two cell lines were stained with 1 µg/ml DAPI (4,6-diamino-2-phenylndole, Invitrogen, #D1306) and 1 µg/ml AO (Acridine Orange, SigmaAldrich, #A-6014) prior to mounting on a microscope slide. Samples were imaged at 2 times magnification using the dark field channel of a NucleoCounter NC-3000 (Chemometec).

Results.

MCF-7 and Jurkat cells were imaged using dark field illumination at low magnification (FIGS. 10 and 13). Based on the dark field images cell sizes were measured by the NucleoView NC-3000 image analysis software. MCF-7 cells were found to be approximately twice as large as Jurkat cells. The average size of MCF-7 cells was estimated to be 53.6 pixels, whereas Jurkat cells were found to be 26.3 pixels in average (FIGS. 11 and 15). This size difference was confirmed by conventional bright field microscopy at high magnification (60×).

To conclude, dark field imaging at low magnification can be used for measuring cell sizes. In this example the sizes are given in pixels. However, after a calibration, the pixel size can be transformed to a physical unit, e.g. µm².

Example 3

Dark Field Imaging can be Used for Discriminating Between Different Cell Types in Mixed Populations Materials and Methods. MCF-7 (ATTC HTB-22) and Jurkat (A3, ATCC-CRL-2570) cells were cultivated at 37° C. in a humidified air atmosphere with 5% $CO_2$ in RPMI (Invitrogen, #61870)+10% FCS (Invitrogen, #10108-165) in T25 flasks. Jurkat cells were harvested at a density of $3.5 \times 10^6$ cells/ml and diluted to a density of $1.7 \times 10^6$ cells/ml. MCF-7 cells were harvested at 75% confluency with 0.5 ml of trypsin (Invitrogen, #25300) and diluted to a density of $1.7 \times 10^6$ cells/ml with medium (RPMI 10% FCS). The two cell lines were mixed 1:1 and stained with 1 µg/ml DAPI (4,6-diamino-2-phenylndole, Invitrogen, #D1306) and 1 µg/ml AO (Acridine Orange, SigmaAldrich, #A-6014) prior to mounting on a microscope slide.

The mixture of MCF-7 and Jurkat cells were imaged at 2 times magnification using a NucleoCounter NC-3000 (Chemometec). DAPI stained cells (dead cells) were detected by exciting the fluorochrome at 365 nm and collecting the emitted blue light (415-525 nm). AO stained cells (total cells) were detected by exciting the fluorochrome at 475 nm and collecting the emitted green light (520-595 nm). The AO and DAPI stained samples were furthermore imaged with a dark field channel (white LED, 400-700 nm) to identify all cells in the populations.

Results.

MCF-7 and Jurkat cells were mixed 1:1 and stained with DAPI and AO. Using a NucleoCounter NC-3000 the mixed cell population was imaged at low magnification. Total cells (living and dead) were detected using either dark field illumination or by measuring the green fluorescence emitted from AO (FIGS. 16 and 17). Dead cells were detected by measuring the blue light emitted from DAPI (FIG. 18). Based on the dark field images cell sizes were measured by the NucleoView NC-3000 image analysis software. FIGS. 20 and 21 clearly demonstrate the presence of two major populations in the mixed sample; one population with an average size of 26.5 pixels and another population with an average size of 53.3 pixels. Combining this information with the observations from example 2 it is unambiguous that the small-sized population represents Jurkat cells, whereas the other major population with larger size represents MCF-7 cells.

To conclude, dark field imaging at low magnification can be used for measuring cell sizes and this information can be utilized for discriminating between different cells types in mixed samples, e.g. blood, lymph, semen and milk.

The invention claimed is:

1. An apparatus for analysing a sample comprising particles and wherein said analysis is performed at low magnification, said apparatus comprises
   At least one dark field light source, comprising at least one light source for emitting light rays, at least one light guide for guiding the light rays emitted from the light source along a first light path, the at least one light guide having a proximal end adjacent the light source and a distal end, at least one light directing device adjacent the distal end of the at least one light guide for deflecting light rays guided by the light guide along a second light path to a sample area of a microscope, and a blocking screen for blocking light rays emitted from the light source which are not guided by the light guide and for partially blocking light rays which are deflected by the light directing device, wherein the blocking screen is positioned at least partially in the second light path and located close to the distal end of the light guide,
   At least one other light source,
   An image sensor for obtaining images of a sample, and
   Magnifying means capable of projecting an image of the particles on the image sensor at a magnification below 10:1,
   wherein light in said at least one dark field light source and said at least one other light source is obtained from LED or a laser diode.

2. The apparatus according to claim 1, wherein said at least one other light source is used in combination with a spectral filter resulting in a fluorescence image.

3. The apparatus according to claim 1, wherein said apparatus comprises or is connected to a system capable of performing image analysis, wherein said image analysis is performed in respect of
   at least two images obtained by dark field analysis or
   at least one image obtained by dark field analysis and at least one image obtained by fluorescence analysis.

4. The apparatus according to claim 3, wherein said apparatus is operative so that at least one image obtained by dark field analysis and at least one image obtained by fluorescence analysis are paired in the image analysis system such that
   particles with at least one predetermined feature are identified in one of the techniques of dark field analysis or fluorescence analysis, and
   these identified particles with at least one predetermined feature are discriminated when performing an image analysis of at least one image obtained with the other of the techniques of dark field analysis or fluorescence analysis.

5. The apparatus according to claim 4, wherein particles to be discriminated are identified in dark field analysis or in fluorescence analysis.

6. The apparatus according to claim 1, wherein the apparatus has a light source rack for placement of at least two light source units.

7. The apparatus according to claim 1, further comprising a spectral filter located between said at least one dark field light source or said at least one other light source and said image sensor.

8. The apparatus according to claim 7, wherein said at least one spectral filter permits light of a wavelength between 200 to 1200 nm to pass through said at least one spectral filter.

9. The apparatus according to claim 8, wherein the dark field light source does not substantially emit light with a wavelength below 700 nm, or wherein the light emitted by said dark field light source is filtered to exclude light with a wavelength below 700 nm from being emitted onto the sample.

10. The apparatus according to claim 9, wherein the numerical aperture of the imaging system is below 0.1.

11. The apparatus according to claim 1, wherein the blocking screen is located directly below the sample.

12. The apparatus according to claim 1, wherein the light rays are non-collimated.

13. A method of analyzing a sample comprising particles, said method comprising the steps of
   Obtaining a sample comprising at least one particle,
   Obtaining at least one dark field image at a magnification below 10:1, using a dark field light source comprising at least one light source for emitting light rays, at least one light guide for guiding the light rays emitted from the light source along a first light path, the at least one light guide having a proximal end adjacent the light source and a distal end, at least one light directing device adjacent the distal end of the at least one light guide for deflecting light rays guided by the light guide along a second light path to a sample area of a microscope, and a blocking screen for blocking light rays emitted from the light source which are not guided by the light guide and for partially blocking light rays which are deflected by the light directing device, wherein the blocking screen is positioned at least partially in the second light path and located close to the distal end of the light guide,
   Obtaining at least one fluorescence image at a similar magnification as used in respect of said at least one dark field image,
   Analyzing the at least one dark field image to obtain information in respect of the particles of the sample,
   Analyzing the at least one fluorescence image to obtain information in respect of the particles of the sample,
   Pairing information obtained from the dark field image and from the fluorescence image,
   wherein said at least one dark field image and said at least one fluorescence image are obtained by the use of an LED or laser diode as a light source.

14. The method according to claim 13, wherein said method comprises image analysis of said at least one dark field image and of said at least one fluorescence image.

15. The method according to claim 14, wherein said image analysis is performed in respect of at least two images obtained by dark field analysis or at least one image obtained by dark field analysis and at least one image obtained by fluorescence analysis.

16. The method according to claim 13, wherein said at least one image obtained by dark field analysis and at least one image obtained by fluorescence analysis are paired in the image analysis system such that
- particles with at least one predetermined feature are identified in one of the techniques of dark field analysis or fluorescence analysis, and
- these identified particles with at least one predetermined feature are discriminated or selected when performing an image analysis of at least one image obtained with the other of the techniques dark field or fluorescence.

17. The method according to claim 13, wherein particles are discriminated based on at least one of: cell size, cell viability, presence or absence of a marker, morphological features of particles, cell membrane integrity, cell wall integrity, or cell division progress.

18. The method according to claim 13, wherein the position, and optionally size, of at least one particle is identified in a dark-field image, and the position, and optionally size, is used to quantify the level of fluorescent signal in the fluorescent image, where said particle is located.

19. The method according to claim 13, wherein two or more dark field images are obtained in respect of different wavelengths of the light rays, or of different incident angles of the light rays.

20. The method according to claim 13, wherein the magnification is a linear magnification at or below 10:1.

21. The method according to claim 13, wherein said particles are in a liquid sample.

22. The method according to claim 13, wherein image analysis of the at least one dark field image and the at least one fluorescence image is used for determination of one or more of the features of the particles selected from the group of
- number of particles,
- concentration of the particles,
- size of the particles,
- size distribution of the particles,
- morphological measurements of the particles,
- cell membrane or cell wall integrity or cell division progress,
- viability of populations of cells or cell parts,
- frequency of particles carrying a specific marker,
- quantifying weak fluorescence signals of particles
- mobility, including speed and directionality.

23. The method according to claim 13, wherein the sample is a biological sample.

24. The method according to claim 13, wherein the particles are cells or cell parts.

25. The method according to claim 13, wherein the blocking screen is located directly below the sample.

26. The method according to claim 13, wherein the light rays are non-collimated.

27. A dark field light source unit for use in microscopy with a magnification below 10:1, said light source unit comprises
- at least one light source for emitting light rays,
- at least one light guide for guiding the light rays emitted from the light source along a first light path, the at least one light guide having a proximal end adjacent the light source and a distal end,
- at least one light directing device adjacent the distal end of the at least one light guide for deflecting light rays guided by the light guide along a second light path to a sample area of a microscope,
- a blocking screen for blocking light rays emitted from the light source which are not guided by the light guide and for partially blocking light rays which are deflected by the light directing device, wherein the blocking screen is positioned at least partially in the second light path and located close to the distal end of the light guide.

28. The light source unit according to claim 27, wherein said light guide is selected from the group of a hollow reflecting light guide, a polymer light guide, a glass light guide.

29. The light source unit according to claim 27, wherein the body of the hollow reflecting light guide is made of metal selected from the group of aluminium, stainless steel, titanium, nickel, copper or brass.

30. The light source unit according to claim 27, wherein the surface of the light guide has a large reflectance.

31. The light source unit according to claim 27, wherein said light directing device deflects the light rays, such that the light rays have an incidence angle selected between angles of 5° to 85° at the sample area.

32. The light source unit according to claim 27, wherein the diameter of said blocking screen and the distance from the blocking screen to the sample area determines an incidence angle such that increasing the diameter of the blocking screen results in an increased incidence angle.

33. The light source unit according to claim 27, wherein said light source is selected from the group of a light emitting diode (LED), a laser diode, a halogen light bulb, a Xenon light bulb, a Mercury light bulb, and a incandescent Tungsten filament light bulb.

34. The light source according to claim 27, wherein radiation with a wavelength below 700 nm is substantially not emitted past the blocking screen.

35. The light source unit according to claim 27, wherein said light guide guides the light rays from the light source in an angle of at least 5° measured from an axis from the position of the light source to a sample compartment.

36. The light source unit according to claim 27, wherein said light directing device deflects the light rays, such that the light rays have an incidence angle selected between angles of about 5° to 85° at the sample area.

37. The light source unit according to claim 27, wherein said light directing device deflects the light rays, such that the light rays have an incidence angle at least of 5°.

38. The light source unit according to claim 27, wherein the diameter of said blocking screen and the distance from the blocking screen to the sample area determines an incidence angle such that increasing the diameter of the blocking screen results in an increased incidence angle.

39. The light source unit according to claim 27, wherein the construction of the light guide is such that the light rays emitted from the light source form the pointed part of a cone.

40. The light source unit according to claim 27, wherein the light directing device is constructed such that it deflects light rays and such that the deflected light rays form the pointing part of a cone.

41. The light source unit according to claim 27, wherein the height of said light guide is less than 30 mm and where the height is measured along an axis from the position of the light source to a sample compartment which is illuminated by deflected light rays.

42. The light source unit according to claim 27, wherein the blocking screen is configured to be placed directly below a sample.

43. The light source unit according to claim 27, wherein the light rays are non-collimated.

44. An apparatus for analysing a sample comprising particles and wherein said analysis is performed at low magnification, said apparatus comprises:
- At least one dark field light source, comprising at least one light source for emitting light rays, at least one light guide for guiding the light rays emitted from the light source along a first light path, the at least one light guide having a proximal end adjacent the light source and a distal end, at least one light directing device adjacent the distal end of the at least one light guide for deflecting light rays guided by the light guide along a second light path to a sample area of a microscope, and a blocking screen for partially blocking light rays which are deflected by the light directing device, wherein the blocking screen is positioned at least partially in the second light path and located close to the distal end of the light guide, At least one other light source, An image sensor for obtaining images of a sample, and Magnifying means capable of projecting an image of the particles on the image sensor at a magnification below 10:1, wherein light in said at least one dark field light source and said at least one other light source is obtained from LED or a laser diode.

45. A method of analyzing a sample comprising particles, said method comprising the steps of:

Obtaining a sample comprising at least one particle,

Obtaining at least one dark field image at a magnification below 10:1 using a dark field light source comprising at least one light source for emitting light rays, at least one light guide for guiding the light rays emitted from the light source along a first light path, the at least one light guide having a proximal end adjacent the light source and a distal end, at least one light directing device adjacent the distal end of the at least one light guide for deflecting light rays guided by the light guide along a second light path to a sample area of a microscope, and a blocking screen for partially blocking light rays which are deflected by the light directing device, wherein the blocking screen is positioned at least partially in the second light path and located close to the distal end of the light guide, Obtaining at least one fluorescence image at a similar magnification as used in respect of said at least one dark field image, Analyzing the at least one dark field image to obtain information in respect of the particles of the sample, Analyzing the at least one fluorescence image to obtain information in respect of the particles of the sample, Pairing information obtained from the dark field image and from the fluorescence image, wherein said at least one dark field image and said at least one fluorescence image are obtained by the use of an LED or laser diode as a light source.

46. A dark field light source unit for use in microscopy with a magnification below 10:1, said light source unit comprises:

at least one light source for emitting light rays;

at least one light guide for guiding the light rays emitted from the light source along a first light path, the at least one light guide having a proximal end adjacent the light source and a distal end;

at least one light directing device adjacent the distal end of the at least one light guide for deflecting light rays guided by the light guide along a second light path to a sample area of a microscope; and a blocking screen for partially blocking light rays which are deflected by the light directing device, wherein the blocking screen is positioned at least partially in the second light path and located close to the distal end of the light guide.

47. The apparatus according to claim 44, wherein the blocking screen is located directly below the sample area of the microscope in use with a microscope.

48. The method according to claim 45, wherein the blocking screen is located directly below the sample area of the microscope in use with a microscope.

49. The light source unit according to claim 46, wherein the blocking screen is configured to be placed directly below a sample area of the microscope in use with a microscope.

* * * * *